US011555055B2

(12) United States Patent
Leissring

(10) Patent No.: US 11,555,055 B2
(45) Date of Patent: Jan. 17, 2023

(54) PEPTIDE INHIBITORS OF INSULIN-DEGRADING ENZYME

(71) Applicant: The Regents of the University of California, Oakland, CA (US)

(72) Inventor: Malcolm A. Leissring, Laguna Beach, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/641,995

(22) PCT Filed: Sep. 11, 2018

(86) PCT No.: PCT/US2018/050508
§ 371 (c)(1),
(2) Date: Feb. 25, 2020

(87) PCT Pub. No.: WO2019/055431
PCT Pub. Date: Mar. 21, 2019

(65) Prior Publication Data
US 2020/0354407 A1    Nov. 12, 2020

Related U.S. Application Data

(60) Provisional application No. 62/557,662, filed on Sep. 12, 2017.

(51) Int. Cl.
| | |
|---|---|
| *C07K 7/64* | (2006.01) |
| *C07K 7/06* | (2006.01) |
| *C07K 7/08* | (2006.01) |
| *C07K 14/81* | (2006.01) |
| *A61P 3/10* | (2006.01) |
| *A61P 17/02* | (2006.01) |
| *A61K 8/64* | (2006.01) |
| *A61K 38/08* | (2019.01) |
| *A61K 38/10* | (2006.01) |
| *A61K 38/12* | (2006.01) |
| *A61K 45/06* | (2006.01) |
| *A61Q 19/08* | (2006.01) |
| *A61K 38/55* | (2006.01) |
| *A61K 38/00* | (2006.01) |

(52) U.S. Cl.
CPC ............ *C07K 7/64* (2013.01); *A61K 8/64* (2013.01); *A61K 38/08* (2013.01); *A61K 38/10* (2013.01); *A61K 38/12* (2013.01); *A61K 38/55* (2013.01); *A61K 45/06* (2013.01); *A61P 3/10* (2018.01); *A61P 17/02* (2018.01); *A61Q 19/08* (2013.01); *C07K 7/06* (2013.01); *C07K 7/08* (2013.01); *C07K 14/81* (2013.01); *A61K 38/00* (2013.01)

(58) Field of Classification Search
CPC ........ A61K 38/12; A61K 38/10; A61K 38/08; A61K 38/55; A61K 38/16; C07K 7/06; C07K 7/08; C07K 14/81
See application file for complete search history.

(56) References Cited

U.S. PATENT DOCUMENTS

| | | | |
|---|---|---|---|
| 10,239,923 B2 * | 3/2019 | Willbold | A61K 38/10 |
| 2002/0168711 A1 | 11/2002 | Rosen et al. | |
| 2004/0158891 A1 | 8/2004 | Thompson et al. | |
| 2012/0028894 A1 | 2/2012 | Frenkel et al. | |
| 2017/0101442 A1 * | 4/2017 | Cheng | C07K 7/08 |

FOREIGN PATENT DOCUMENTS

| | | | | |
|---|---|---|---|---|
| WO | WO-2016150416 A1 * | 9/2016 | | A61K 38/10 |
| WO | WO 2016/172631 A2 | 10/2016 | | |

OTHER PUBLICATIONS

Hussong "Sterile Products: Advances and Challenges in Formulation, Manufacturing and Regulatory Aspects—A Regulatory Review Perspective", AAPS PharmSciTech, 2010, pp. 1482-1484 (Year: 2010).*
Cabrele et al. "Peptides Containing B-Amino Acid Patterns: Challenges and Successes in Medicinal Chemistry", Journal of Medicinal Chemistry, 2014, pp. 9718-9739 (Year: 2014).*
Di Gioia et al. "N-methylated a-Amino Acids and Peptides: Synthesis and Biological Activity", Mini-Reviews in Medicinal Chemistry, 2016, pp. 683-690 (Year: 2016).*
Merriam-Webster, (n.d.). Correspond. In Merriam-Webster.com dictionary. Retrieved May 25, 2022, from https://www.merriam-webster.com/dictionary/correspond (Year: 2022).*
PCT International Search Report and Written Opinion dated Feb. 6, 2019 issued in PCT/US18/50508.
PCT International Preliminary Report on Patentability dated Mar. 17, 2020 issued in PCT/US2018/050508.
European Partial Supplementary Search Report dated Jun. 4, 2021 issued in EP 18857213.5.
Aaronson, et al. (1990) "Growth factor-regulated pathways in epithelial cell proliferation," *Am. Rev. Respir. Dis.* 142: S7-S10.
Abdul-Hay, et al. (2011)"Deletion of insulin-degrading enzyme elicits antipodal, age-dependent effects on glucose and insulin tolerance." *Plos. One* 6(6): e20818 [6 pages].
Abdul-Hay, et al. (2013) "Optimization of peptide hydroxamate inhibitors of insulin-degrading enzyme reveals marked substrate-selectivity." *J. Med. Chem.* 56: 2246-2255.
Abdul-Hay, et al. (2015) "Selective targeting of extracellular insulindegrading enzyme by quasi-irreversible thiol-modifying inhibitors." *ACS Chem. Biol.* 10, 2716-2724.

(Continued)

*Primary Examiner* — Lianko G Garyu
(74) *Attorney, Agent, or Firm* — Emily M. Haliday; Weaver Austin Villeneuve & Sampson LLP

(57) ABSTRACT

The present disclosure describes novel peptides, including peptides that inhibit the proteolytic activity of insulin-degrading enzyme (IDE). Also described are cosmetic and pharmaceutical formulations including these peptides, as well as a treatment method aimed at improving the appearance and/or texture of skin and/or promoting wound healing and a method for treating diabetes. The disclosed peptides and formulations are particularly useful for addressing the problem of impaired wound healing in diabetes.

25 Claims, 15 Drawing Sheets

Specification includes a Sequence Listing.

(56) References Cited

OTHER PUBLICATIONS

Apikoglu-Rabus, et al. (2010) "Effect of topical insulin on cutaneous wound healing in rats with or without acute diabetes." *Clin. Exp. Dermatol.* 35: 180-185.
Aust, et al. (2008) "Percutaneous collagen induction therapy: an alternative treatment for scars, wrinkles, and skin laxity." *Plast. Reconstr. Surg.* 121: 1421-1429.
Baltzis, et al. (2014) "Pathogenesis and treatment of impaired wound healing in diabetes mellitus: new insights." *Adv. Ther.* 31: 817-836.
Bannister, et al. (2010) "MT345, A Small-Molecule Inhibitor of the Insulin-Degrading Enzyme (IDE)." *Probe Reports from the NIH Molecular Libraries Program*, 32 pages.
Belfield, et al. (1970) "The use of insulin in open-wound healing." *Vet. Med. Small Anim. Clin.* 65: 455-460.
Benoliel, et al. (1997) "Insulin stimulates haptotactic migration of human epidermal keratinocytes through activation of NF-kappa B transcription factor." *J. Cell Sci.* 110: 2089-2097.
Cabrol, et al. (2009) "Small-molecule activators of insulin-degrading enzyme discovered through high-throughput compound screening." *Plos. One* 4(4): e5274 [8 pages].
Cechowska-Pasko, et al. (2009) "The effect of glucose deprivation on collagen synthesis in fibroblast cultures" *Mol Cell Biochem.* 327(1-2):211-8.
Charton, et al. (2014) "Imidazole-derived 2-[N-carbamoylmethyl-alkylamino]acetic acids, substrate-dependent modulators of insulin-degrading enzyme in amyloid-beta hydrolysis." *Eur. J. Med. Chem.* 79: 184-193.
Charton, et al. (2015) "Structure-activity relationships of imidazole-derived 2-[N-carbamoylmethyl-alkylamino]acetic acids, dual binders of human insulin-degrading enzyme." *Eur. J. Med. Chem.* 90: 547-567.
Cheng and Prusoff (1973) "Relationship between the inhibition constant (K1) and the concentration of inhibitor which causes 50 per cent inhibition (I50) of an enzymatic reaction," *Biochem. Pharmacol.* 22: 3099-3108.
Coid, D. R. (1977) "Hypoglycaemia during treatment of decubitus ulcer with topical insulin," *Br. Med. J.* 2: 1063-1064.
Delledonne, et al. (2009) "Development of monoclonal antibodies and quantitative ELISAs targeting insulin-degrading enzyme." *Mol. Neurodegen.* 4: 39 [6 pages].
Duckworth, et al. (2004) "Insulin-degrading activity in wound fluid." *J. Clin. Endocrinol. Metab.* 89: 847-851.
Durham, et al. (2015) "Dual exosite-binding inhibitors of insulin-degrading enzyme challenge its role as the primary mediator of insulin clearance in vivo." *J. Biol. Chem.* 290(33): 20044-20059.
Farris, et al. (2003) "Insulin-degrading enzyme regulates the levels of insulin, amyloid beta-protein, and the beta-amyloid precursor protein intracellular domain in vivo." *Proc. Natl. Acad. Sci. U.S.A.* 100: 4162-4167.
Farris, et al. (2005) "Alternative splicing of human insulin-degrading enzyme yields a novel isoform with a decreased ability to degrade insulin and amyloid beta-protein," *Biochemistry* 44: 6513-6525.
Fernandes, D. (2005) "Minimally invasive percutaneous collagen induction." *Oral Maxillofac. Surg. Clin. North Am.* 17: 51-63.
Goldstein, et al. (1989) "Stimulation of collagen formation by insulin and insulin-like growth factor I in cultures of human lung fibroblasts." *Endocrinology* 124(2): 964-970.
Gordon and Hahn (2010) "Collagens" *Cell Tissue Res.* 339: 247-257.
Gore-Hyer, et al. (2003) "Selective stimulation of collagen synthesis in the presence of costimulatory insulin signaling by connective tissue growth factor in scleroderma fibroblasts." *Arthritis Rheum.* 48(3): 798-806.
Greenway, et al. (1999) "Topical insulin in wound healing: a randomised, double-blind, placebo-controlled trial." *J. Wound Care* 8: 526-528.

Hanam, et al. (1983) "The effect of topical insulin on infected cutaneous ulcerations in diabetic and nondiabetic mice." *J. Foot Surg.* 22: 298-301.
Hrynyk, et al. (2014) "Insulin and wound healing," *Burns* 40: 1433-1446.
Im, et al. (2007) "Structure of substrate-free human insulin-degrading enzyme (IDE) and biophysical analysis of ATP-induced conformational switch of IDE." *J. Biol. Chem.* 282: 25453-25463.
Kjellstrom, et al. (1984) "Insulin effects on collagen and protein production in cultured human skin fibroblasts from diabetic and non-diabetic subjects." *Horm. Metab. Res.* 16: 168-171.
Krupsky, et al. (1996) "Regulation of type I collagen production by insulin and transforming growth factor-beta in human lung fibroblasts." *Connect. Tissue Res.* 34: 53-62.
Kuo, et al. (1993) "Insulin-degrading enzyme is differentially expressed and developmentally regulated in various rat tissues." *Endocrinology* 132(2): 604-611.
Leal and Morelli (2013) "Insulysin" *Handbook of Proteolytic Enzymes, Clan ME-M16A—Chapter 318*; pp. 1415-1420.
Leissring and Selkoe (2006) "Structural biology: enzyme target to latch on to." *Nature* 443: 761-762.
Leissring et al. (2021) "Targeting Insulin-Degrading Enzyme in Insulin Clearance" *International Journal of Molecular Sciences* 22: 2235 (21 pages).
Leissring, et al. (2003) "Kinetics of amyloid beta-protein degradation determined by novel fluorescence- and fluorescence polarization-based assays." *J. Biol. Chem.* 278: 37314-37320.
Leissring, et al. (2010) "Designed inhibitors of insulin-degrading enzyme regulate the catabolism and activity of insulin." *Plos. One* 5: e10504 (13 pages).
Liang, et al. (2007) "In vitro scratch assay: a convenient and inexpensive method for analysis of cell migration in vitro," *Nat. Protoc.* 2(2): 329-333.
Lima, et al. (2012) "Topical insulin accelerates wound healing in diabetes by enhancing the AKT and ERK pathways: a double-blind placebo-controlled clinical trial." *Plos. One* 7(5): e36974 (13 pages).
Liu, et al. (2009) "Cell and molecular mechanisms of keratinocyte function stimulated by insulin during wound healing," *BMC Cell Biol.* 10: 1 (15 pages).
Madibally, et al. (2003) "Influence of insulin therapy on burn wound healing in rats." *J. Surg. Res.* 109: 92-100.
Maianti, et al. (2014) "Anti-diabetic activity of insulin-degrading enzyme inhibitors mediated by multiple hormones." *Nature* 511(7507): 94-98 [15 pages].
Miller, et al. (2003) "Amyloid-beta peptide levels in brain are inversely correlated with insulysin activity levels in vivo." *Proc. Natl. Acad. Sci. U.S.A.* 100: 6221-6226.
Mirsky and Perisutti (1955) "Effect of insulinase-inhibitor on hypoglycemic action of insulin." *Science* 122: 559-560.
Mirsky, et al. (1955) "Effect of insulinase-inhibitor on destruction of insulin by intact mouse." *Proc. Soc. Exp. Biol. Med.* 88: 76-78.
Monaco, et al. (2009) "Insulin stimulates fibroblast proliferation through calcium-calmodulin-dependent kinase II." *Cell Cycle* 8(13): 2024-2030.
Musselmann, et al. (2006) Stimulation of collagen synthesis by insulin and proteoglycan accumulation by ascorbate in bovine keratocytes in vitro. *Invest. Ophthalmol. Vis. Sci.* 47, 5260-5266.
Neant-Fery, et al. (2008) "Molecular basis for the thiol sensitivity of insulin-degrading enzyme." *Proc. Natl. Acad. Sci. U.S.A.* 105(28): 9582-9587.
Rezvani, et al. (2009) "A randomized, double-blind, placebo-controlled trial to determine the effects of topical insulin on wound healing." *Ostomy. Wound Manage.* 55: 22-28.
Shearer, et al. (1997) "Insulin is degraded extracellularly in wounds by insulin-degrading enzyme (EC 3,4.24.56)." *Am. J. Physiol.* 273: E657-664.
Shen, et al. (2006) "Structures of human insulin-degrading enzyme reveal a new substrate recognition mechanism," *Nature* 443: 870-874.
Smith, G. P. (1985) "Filamentous fusion phage: novel expression vectors that display cloned antigens on the virion surface." *Science* 228: 1315-1317.

(56) References Cited

OTHER PUBLICATIONS

Suire et al. (2018) "Peptidic inhibitors of insulin-degrading enzyme with potential for dermatological applications discovered via phage display" *Plos. One* 13(2): e0193101 (16 pages).
Tang, W. J. (2016) "Targeting Insulin-Degrading Enzyme to Treat Type 2 Diabetes Mellitus." *Trends Endocrinol. Metab.* 27: 24-34 [HHS Public Access—Author Manuscript—19 pages].
Trevisan, et al. (1997) "Enhanced collagen synthesis in cultured skin fibroblasts from insulin-dependent diabetic patients with nephropathy." *J. Am. Soc. Nephrol.* 8: 1133-1139.
Villee and Powers (1977) "Effect of glucose and insulin on collagen secretion by human skin fibroblasts in vitro," *Nature* 268: 156-158.
Weringer, et al. (1982) "Effects of insulin on wound healing in diabetic mice." *Acta Endocrinol. (Copenh.)* 99: 101-108.
Wertheimer, et al. (2000) "Differential roles of insulin receptor and insulin-like growth factor-1 receptor in differentiation of murine skin keratinocytes." *J. Invest. Dermatol.* 115: 24-29.
Wertheimer, et al. (2001) "The regulation of skin proliferation and differentiation in the IR null mouse: implications for skin complications of diabetes." *Endocrinology* 142(3): 1234-1241.
Wilson, et al. (2008) "A role for topical insulin in the management problematic surgical wounds." *Ann. R. Coll. Surg. Engl.* 90: 160 (1 page).
Singh and Yadav (2016) "Microneedling: Advances and widening horizons." Indian Dermatol. Online J. 7: 244-254.

\* cited by examiner

Ph.D.-C7C

| Clone | AA Sequence | Sequence ID NO |
|---|---|---|
| Seq-C7C-01 | CNWMNIHMC | 25 |
| Seq-C7C-02 | CSKNFPRNC | 26 |
| Seq-C7C-03 | CDWMRIWNC | 27 |
| Seq-C7C-04 | CIHSPTALC | 28 |
| Seq-C7C-05 | CLPWPLSLC | 29 |
| Seq-C7C-06 | CSWWMLHHC | 30 |
| Seq-C7C-07 | CSWWNIHLC | 31 |
| Seq-C7C-08 | CLWWQLHLC | 32 |
| Seq-C7C-09 | CSWMSIHLC | 33 |
| Seq-C7C-10 | CGFTTTFVC | 34 |
| Seq-C7C-11 | CSWWNIHLC | 31 |
| Seq-C7C-12 | CNAGHLSQC | 35 |
| Seq-C7C-13 | CSWMSIHLC | 33 |
| Seq-C7C-14 | CSWMSIHLC | 33 |
| Seq-C7C-15 | CSWWSIHVC | 36 |
| Seq-C7C-16 | CLLLLNNTC | 37 |
| Seq-C7C-17 | CNWWTIHNC | 38 |
| Seq-C7C-18 | CNSIKKWSC | 39 |
| Seq-C7C-19 | CNAGHLSQC | 35 |
| Seq-C7C-20 | CISSSINHC | 40 |

| | Sequence ID NO |
|---|---|
| C S W M S I H L C | 33 |
| C S W M S I H L C | 33 |
| C S W M S I H L C | 33 |
| C S W W S I H V C | 36 |
| C S W W N I H L C | 31 |
| C S W W N I H L C | 31 |
| C N W M N I H M C | 25 |
| C N W W T I H N C | 38 |
| C S W W M L H H C | 30 |
| C L W W Q L H L C | 32 |
| C S K N F P R N C | 26 |
| C D W M R I W N C | 27 |
| C I H S P T A L C | 28 |
| C L P W P L S L C | 29 |
| C G F T T T F V C | 34 |
| C N A G H L S Q C * | 35 |
| C N A G H L S Q C * | 35 |
| C L L L L N N T C | 37 |
| C N S I K K W S C | 39 |
| C I S S S I N H C | 40 |
| C S W W S I H L C | 41 |

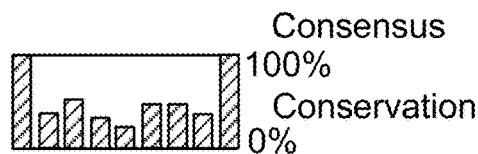

Consensus
100%
Conservation
0%

FIG. 1B

| Peptide Name | Peptide Sequence | Sequence ID NO | Repeats (among 20) | Prevalence (%) |
|---|---|---|---|---|
| C7C-1 | ACSWWSIHLCG | 3 | consensus | consensus |
| C7C-2 | ACNAGHLSQCG | 8 | 2 | 10.0 |

| Clone | AA Sequence | Sequence ID NO |
|---|---|---|
| Seq-12A-01 | VHWDFRQWWQPS | 2 |
| Seq-12A-02 | NQLLTQRTPFQD | 42 |
| Seq-12A-03 | SSNVISPFEQLL | 43 |
| Seq-12A-04 | WVPWSTPFWLQQ | 43 |
| Seq-12A-05 | VHWDFRQWWQPS | 2 |
| Seq-12A-06 | VHWDFRQWWQPS | 2 |
| Seq-12A-07 | | |
| Seq-12A-08 | NSPSGLIGWTSR | 44 |
| Seq-12A-09 | WVPWSYEYFVST | 45 |
| Seq-12A-10 | VHWDFRQWWQPS | 2 |
| Seq-12A-11 | VHWDFRQWWQPS | 2 |
| Seq-12A-12 | VHWDFRQWWQPS | 2 |
| Seq-12A-13 | VHWDFRQWWQPS | 2 |
| Seq-12A-14 | VHWDFRQWWQPS | 2 |
| Seq-12A-15 | VHWDFRQWWQPS | 2 |
| Seq-12A-16 | GPYVLGEHLRSN | 46 |
| Seq-12A-17 | VHWDFRQWWQPS | 2 |
| Seq-12A-18 | VHWDFRQWWQPS | 2 |
| Seq-12A-19 | VHWDFRQWWQPS | 2 |
| Seq-12A-20 | VHWDFRQWWQPS | 2 |

| Clone | AA Sequence | Sequence ID NO |
|---|---|---|
| Seq-12B-01 | LNFPMPSRPHSS | 12 |
| Seq-12B-02 | VHWDFRQWWQPS | 2 |
| Seq-12B-03 | VHWDFRQWWQPS | 2 |
| Seq-12B-04 | VHWDFRQWWQPS | 2 |
| Seq-12B-05 | LNFPMPSRPHSS | 12 |
| Seq-12B-06 | LNFPMPSRPHSS | 12 |
| Seq-12B-07 | SPLWSGWALEIL | 47 |
| Seq-12B-08 | SFTWLHGSLTER | 48 |
| Seq-12B-09 | VHWDFRQWWQPS | 2 |
| Seq-12B-10 | WSPISGKFFQRF | 4 |
| Seq-12B-11 | LNFPMPSRPHSS | 12 |
| Seq-12B-12 | SNTQNVYWERWI | 49 |
| Seq-12B-13 | QSLPWCYPHCVT | 1 |
| Seq-12B-14 | RFPGPIEPDLRF | 50 |
| Seq-12B-15 | WSPISGKFFQRF | 4 |
| Seq-12B-16 | VHWDFRQWWQPS | 2 |
| Seq-12B-17 | VHWDFRQWWQPS | 2 |
| Seq-12B-18 | QSLPWCYPHCVT | 1 |
| Seq-12B-19 | QSLPWCYPHCVT | 1 |
| Seq-12B-20 | LNFPMPSRPHSS | 12 |

*FIG. 1E*

| Peptide Name | Peptide Sequence | Sequence ID NO | Repeats (among 20) | Prevalence (%) |
|---|---|---|---|---|
| P12-1 | VHWDFRQWWQPS | 2 | 19 | 48.7 |
| P12-2 | LNFPMPSRPHSS | 12 | 5 | 12.8 |
| P12-3 | QSLPWCYPHCVT | 1 | 3 | 7.7 |
| P12-4 | WSPICGKFFQRF | 51 | 2 | 5.1 |

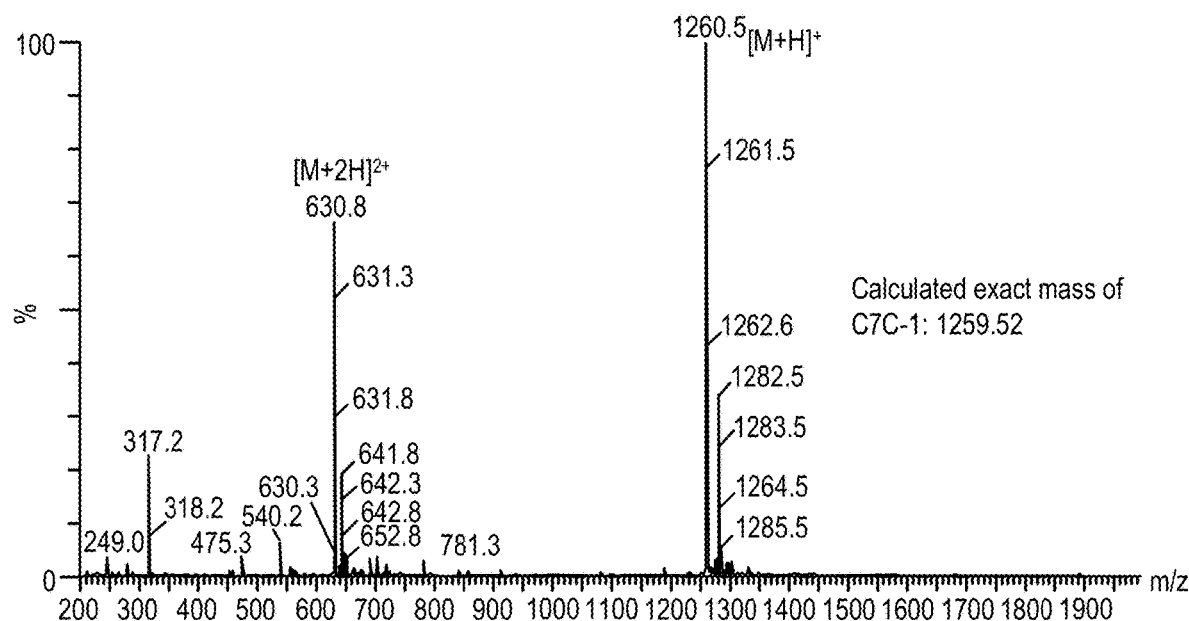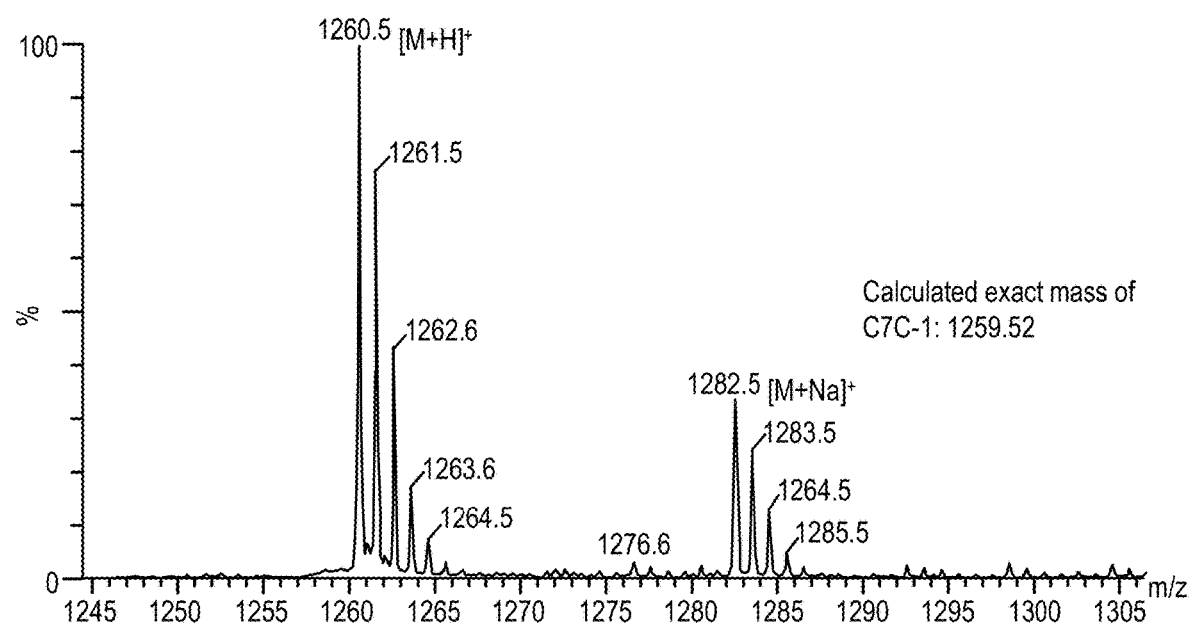
FIG. 6

PEPTIDE INHIBITORS OF INSULIN-DEGRADING ENZYME

CROSS-REFERENCE TO RELATED APPLICATIONS

This application is a U.S. 371 National Phase of PCT/US2018/050508, filed Sep. 11, 2018, which claims benefit of and priority to U.S. Ser. No. 62/557,662, filed on Sep. 12, 2017, which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant No. GM115617, awarded by the National Institutes of Health. The Government has certain rights in this invention.

INCORPORATION BY REFERENCE OF SEQUENCE LISTING PROVIDED AS A TEXT FILE

The instant application contains a Sequence Listing which has been submitted electronically in ASCII format and is hereby incorporated by reference in its entirety. Said ASCII copy, created on Aug. 2, 2021, is named 2021-08-02_UCIRP024US_SeqList_ST25.txt and is 16,597 bytes in size.

FIELD

The present disclosure relates generally to the area of peptide inhibitors of insulin-degrading enzyme. In particular, the disclosure relates to methods and compositions for promoting wound healing, for cosmetic applications and for anti-diabetic applications.

BACKGROUND

Twenty percent of the elderly population, particularly diabetics, have slow-healing or chronic wounds. Current solutions include antibiotic ointments, hyperbaric medicine, and surgeries. Current solutions do not promote the key processes underlying wound healing (e.g., collagen synthesis, keratinocyte mitogenesis and migration, etc.), which are known to be stimulated by peptide hormones such as insulin, insulin-like growth factors (IGFs) and transforming growth factors (TGFs).

In the U.S. alone, over $20 billion per year is spent on skin care products aimed at combatting the effects of aging (e.g., wrinkled skin). Numerous skin care products exist that rely on a variety of methods (hydration, delivery of essential oils and fats, promotion of exfoliation, etc.). Current solutions do not address key processes that maintain healthy skin (healthy levels of collagen synthesis and subcutaneous fat), which are mediated by insulin, IGFs and TGFs and other peptide hormones.

An estimated 384 million people suffer from diabetes mellitus worldwide, at a global economic cost of $619 billion/year. Diabetes also at least doubles the risk of death, causing up to 4.9 million deaths per year. Current solutions include insulin injection and a variety of oral medicaments, including secretagogues and PPAR-gamma activators. Current solutions, however, suffer from key limitations. Not all patients tolerate or comply with all available treatments and some of these drugs have undesirable side-effects including hypoglycemia, diarrhea, and in some instances liver damage.

SUMMARY

The present invention relates to novel peptide inhibitors of insulin-degrading enzyme (IDE), an atypical zinc-metallopeptidase that is the primary catabolizer of insulin, a peptide hormone that plays a central role in the regulation of blood glucose, which is perturbed in diabetes. IDE also degrades other peptide hormones such as insulin-like growth factor-2 (IGF2) and transforming growth factor-alpha (TGF-alpha), which-together with insulin—are key mediators of a variety of physiological processes, particularly collagen synthesis and other aspects of wound repair.

Despite its wide-ranging biomedical significance, only a very limited number of IDE inhibitors have been developed to date. The few inhibitors that have been developed, moreover, are highly experimental in nature and, in particular, their biocompatibility and toxicity remain to be established. The present disclosure provides novel peptides that inhibit IDE potently and selectively. Because these peptides are, in some embodiments, made up entirely of all-natural amino acids, they can be metabolized by the body without concern for toxic side effects. In addition, a subset of the inhibitors are cyclic peptides, which enhances their stability in the biologic milieu.

Various embodiments contemplated herein may include, but need not be limited to, one or more of the following:

Embodiment 1: An isolated peptide or peptoid of, or corresponding to, 30 amino acid residues or less, wherein the peptide includes or consists of a peptide amino acid sequence having at least 80% sequence identity to an amino acid sequence selected from the group consisting of: QSLPWCYPHCVT (SEQ ID NO:1), VHWDFRQWWQPS (SEQ ID NO:2), ACSWWSIHLCG (SEQ ID NO:3), and WSPISGKFFQRF (SEQ ID NO:4); or the peptoid corresponds to said peptide amino acid sequence.

Embodiment 2: The peptide or peptoid of embodiment 1, wherein the peptide or peptoid inhibits the proteolytic activity of insulin-degrading enzyme (IDE).

Embodiment 3: The peptide or peptoid of embodiment 1 or embodiment 2 wherein the peptide or peptoid includes or corresponds to not more than 15 amino acid residues.

Embodiment 4: The peptide or peptoid of any one of embodiments 1-3, wherein the peptide includes all L-isomer amino acid residues.

Embodiment 5: The peptide or peptoid of any one of embodiments 1-3, wherein the peptide includes one or more D-isomer amino acid residues.

Embodiment 6: The peptide or peptoid of any one of embodiments 1-4, wherein the peptide or peptoid is cyclized.

Embodiment 7: The peptide or peptoid of any one of embodiments 1-4, wherein the peptide or peptoid includes a modification other than cyclization that increases stability.

Embodiment 8: The peptide or peptoid of embodiment 7, wherein the peptide is a retro-inverso peptide.

Embodiment 9: The peptide or peptoid of embodiment 7, wherein the peptide includes one or more N-methyl amino acid residues.

Embodiment 10: The peptide or peptoid of any one of embodiments 1-3, wherein the peptide includes one or more beta-amino acid residues.

Embodiment 11: The peptide or peptoid of any one of embodiments 1-10, wherein the peptide bears no terminal protecting groups.

Embodiment 12: The peptide or peptoid of any one of embodiments 1-10, wherein the peptide includes bears one or more terminal protecting groups.

Embodiment 13: The peptide or peptoid of embodiment 12, wherein said one or more protecting groups are independently selected from the group consisting of acetyl, amide, 3 to 20 carbon alkyl groups, fluorenylmethyloxycarbonyl (Fmoc), 9-fluoreneacetyl group, 1-fluorenecarboxylic group, 9-fluorenecarboxylic group, 9-fluorenone-1-carboxylic group, benzyloxycarbonyl, xanthyl (Xan), trityl (Trt), 4-methyltrityl (Mtt), 4-methoxytrityl (Mmt), 4-methoxy-2,3,6-trimethyl-benzenesulphonyl (Mtr), mesitylene-2-sulphonyl (Mts), 4,4-dimethoxybenzhydryl (Mbh), tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimentyl-2,6-diaxocyclohexylidene) ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), benzyloxymethyl (Bom), t-butyloxycarbonyl (Tboc), cyclohexyloxy (cHxO), t-butoxymethyl (Bum), t-butoxy (tBuO), t-butyl (tBu), and trifluoroacetyl (TFA).

Embodiment 14: The peptide or peptoid of embodiment 12 or embodiment 13, wherein peptide includes a protecting group at a carboxyl terminus and/or an amino terminus.

Embodiment 15: The peptide or peptoid of any one of embodiments 12-14, wherein an amino terminus is acetylated.

Embodiment 16: The peptide or peptoid of any one of embodiments 12-15, wherein a carboxyl terminus is amidated.

Embodiment 17: The peptide or peptoid of embodiment 16, wherein the peptide includes or consists of QSLPWCYPHCVT (SEQ ID NO:1), additionally including an amide group at the C-terminus of the peptide.

Embodiment 18: The peptide or peptoid according to any one of embodiments 1-17, wherein said peptide or peptoid is functionalized with a polymer to increase its stability in a biological milieu.

Embodiment 19: The peptide or peptoid of embodiment 18, wherein said polymer includes polyethylene glycol and/or a cellulose or modified cellulose.

Embodiment 20: A cosmetic or pharmaceutical formulation including the peptide or peptoid of any one of embodiments 1-19 and a carrier.

Embodiment 21: The cosmetic or pharmaceutical formulation of embodiment 20, wherein the cosmetic or pharmaceutical formulation is sterile.

Embodiment 22: The cosmetic or pharmaceutical formulation of embodiment 20 or embodiment 21, wherein the formulation is a topical formulation.

Embodiment 23: The cosmetic or pharmaceutical formulation of embodiment 22, wherein the formulation includes an additional active agent that promotes smooth skin or wound healing.

Embodiment 24: The cosmetic or pharmaceutical formulation of embodiment 20 or embodiment 21, which is formulated for systemic administration.

Embodiment 25: The cosmetic or pharmaceutical formulation of embodiment 24, wherein the formulation is an oral or injectable formulation.

Embodiment 26: The cosmetic or pharmaceutical formulation of embodiment 25, wherein the formulation additionally includes active agent that ameliorates at least one symptom of diabetes.

Embodiment 27: A method of improving the appearance and/or texture of skin and/or promoting wound healing in a living subject, wherein the method includes topically administering the peptide or peptoid of any one of embodiments 1-19 or the cosmetic or pharmaceutical formulation according any one of embodiments 20-23 to the skin of the subject.

Embodiment 28: The method of embodiment 27, wherein the method additionally includes administering to the subject an additional formulation including one or more active agents that promote smooth skin or wound healing.

Embodiment 29: A method of treating diabetes, wherein the method includes administering an effective amount of the peptide or peptoid of any one of embodiments 1-19 or any of the cosmetic or pharmaceutical formulations of embodiments 20, 21, or 24-26 to a subject having diabetes.

Embodiment 30: The method of embodiment 29, wherein the method additionally includes administering to the subject an additional formulation including one or more active agents that ameliorate at least one symptom of diabetes.

Embodiment 31: The method of any one of embodiments 27-30, wherein the subject is one who has been diagnosed as having diabetes.

Embodiment 32: The method of any one of embodiments 27-31, wherein the subject is a mammal.

Embodiment 33: The method of embodiment 32, wherein the subject is a non-human mammal.

Embodiment 34: The method of embodiment 32, wherein the subject is a human.

Embodiment 35: The peptide or peptoid of embodiment 1, the cosmetic or pharmaceutical formulation of embodiment 20, or the method of embodiment 27 or embodiment 29, wherein the peptide or peptoid is a peptide.

Embodiment 36: The peptide, cosmetic or pharmaceutical formulation, or method of embodiment 35, wherein the peptide includes or consists of an amino acid sequence selected from the group consisting of: QSLPWCYPHCVT (SEQ ID NO:1), VHWDFRQWWQPS (SEQ ID NO:2), ACSWWSIHLCG (SEQ ID NO:3), and WSPISGKFFQRF (SEQ ID NO:4).

BRIEF DESCRIPTION OF THE DRAWINGS

FIG. 1A-F. Peptides derived by phage display. A, Peptide sequences deduced from DNA sequencing of 20 clones from the Ph.D.™-C7C library. B, Consensus sequence derived from analysis of all data. C, Parent peptides selected for synthesis and testing. C,D, Peptide sequences deduced from DNA sequencing of 39 clones from the Ph.D.™-12 library, conducted as two independent runs (D and E). F, Parent peptides selected for subsequent synthesis and testing based on prevalence.

DETAILED DESCRIPTION

Definitions

Figure 2:
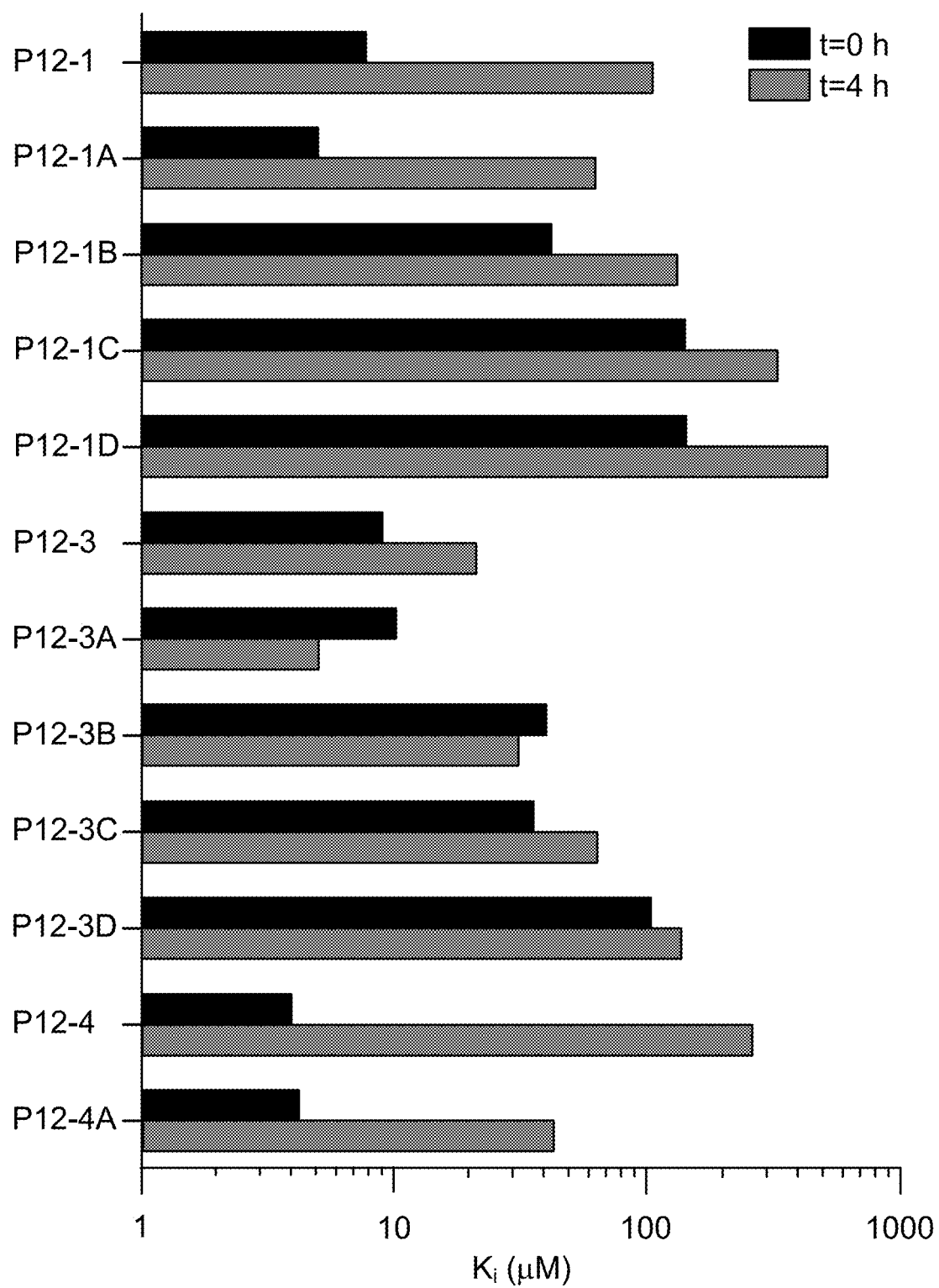
FIG. 2. Vulnerability of peptides to degradation by IDE assessed by activity assays. $IC_{50}$ values obtained for selected peptides pre-incubated with IDE 0 or 4 h before testing with the FRET1 assay. Note that all peptides except those in the P12-3 family showed marked reductions in apparent potency after prolonged incubation with IDE, reflecting degradation. Data are the average of duplicate assays that did not differ by more than 5%.

Terms used in the claims and specification are defined as set forth below unless otherwise specified.

The term "peptide" as used herein refers to a polymer of amino acid residues typically ranging in length from 2 to about 30, or to about 40, or to about 50, or to about 60, or to about 70 residues. In certain embodiments, a peptide ranges in length from about 8, 9, 10, 11, 12, or 13 residues to about 14, 15, 20, 25, or 30 residues. In illustrative embodiments, the peptide has a length falling within the range 2-30, 3-25, 4-20, 5-19, 6-18, 7-17, 8-16, 9-15, 10-14, or 11-13 amino acid residues. In certain embodiments, the amino acid residues of the peptide are "L-isomer" amino acid residues ("L" amino acids); however, in various embodiments, one or more "D-isomer" amino acid residues ("D" amino acid) can be incorporated into the peptide, or the peptide can comprise all "D" amino acids. Peptides also include amino acid polymers in which one or more amino acid residues is an artificial chemical analogue of a corresponding naturally occurring amino acid. In addition, the term applies to amino acids joined by a peptide linkage or by other, "modified linkages" (e.g., where the peptide bond is replaced by an α-ester, a β-ester, a thioamide, phosphoramide, a sulfonamide, a carbonate or carbamate, a hydroxylate, and the like (see, e.g., Spatola, (1983) *Chem. Biochem. Amino Acids and Proteins* 7: 267-357, which is incorporated herein by reference for this description), where the amide is replaced with a saturated amine (see, e.g., Skiles et al., U.S. Pat. No. 4,496,542, Kaltenbronn et al., (1990) Pp. 969-970 in Proc. 11th American Peptide Symposium, ESCOM Science Publishers, The Netherlands, each of which is incorporated herein by reference for this description, and the like).

The term "amino acid residue" as used herein refers to natural, synthetic, or modified amino acids. Various amino acid analogues include, but are not limited to 2-aminoadipic acid, 3-aminoadipic acid, beta-alanine (beta-aminopropionic acid), 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, N-ethylglycine, n-ethylasparagine, hydroxylysine, allo-hydroxylysine, 3-hydroxyproline, 4-hydroxyproline, isodesmosine, allo-isoleucine, n-methylglycine, sarcosine, n-methylisoleucine, 6-n-methyllysine, n-methylvaline, norvaline, norleucine, ornithine, L-2-amino-3-guanidinopropionic acid (AGP), L-α,γ-diaminobutyric acid (DAB), L-α,β-diaminopropionic acid (DAP), L-α-t-butylglycine and the like. These modified amino acid residues are illustrative and not intended to be limiting.

The amino acid residue abbreviations shown in Table 1 are used herein.

TABLE 1

| Amino acid abbreviations. | | |
|---|---|---|
| | Abbreviation | |
| Name | 3 Letter | 1 Letter |
| Alanine | Ala | A |
| βAlanine (NH₂—CH₂—CH₂—COOH) | βAla | |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| episilon-aminocaproic acid (NH²—(CH₂)₅—COOH) | Ahx | J |
| 4-aminobutanoic acid (NH₂—(CH₂)₃—COOH) | γAbu | |
| tetrahydroisoquinoline-3-carboxylic acid | | O |
| Lys(N(epsilon)-trifluoroacetyl) | | K[TFA] |
| α-aminoisobutyric acid | Aib | B |

"Beta-peptides" contain one or more or all "beta-amino acid residues," which have their amino group bonded to the β-carbon rather than the α-carbon as in the 20 standard biological amino acids. The only commonly naturally occurring beta-amino acid is β-alanine.

The term "natural" as applied to peptides herein refers to peptides constituted only of the naturally-occurring amino acids: Ala, Cys, Asp, Glu, Glu, Phe, Gly, His, Ile, Lys, Leu, Met, Asn, Pro, Gln, Arg, Ser, Thr, Val, Trp, and Tyr.

"Peptoids" are a specific subclass of peptidomimetics. They are closely related to their natural peptide counterparts, but differ chemically in that one or more or all side chains are appended to nitrogen atoms along the molecule's backbone, rather than to the α-carbons (as they are in natural amino acids). A peptoid has a monomer sequence that essentially corresponds to that of a natural peptide, where a natural amino acid is replaced by an N-substituted glycine derivative, if the N-substituted glycine derivative resembles the original amino acid in hydrophilicity, hydrophobicity, polarity, etc. The following are illustrative, but non-limiting N-substituted glycine replacements: N-(1-methylprop-1-yl)glycine→isoleucine (I), N-(prop-2-yl)glycine→valine (V), N-benzylglycine→phenylalanine (F), N-(2-hydroxyethyl)glycine→serine (S), and the like. In certain aspects of the invention, substitutions need not be "exact". Thus for example, in certain aspects of the invention, N-(2-hydroxyethyl)glycine may substitute for S, T, C, and/or M; N-(2-methylprop-1-yl)glycine may substitute for V, L, and/or I; N-(2-hydroxyethyl)glycine can be used to substitute for T or S. In general, one may use an N-hydroxyalkyl-substituted glycine to substitute for any polar amino acid, an N-benzyl- or N-aralkyl-substituted glycine to replace any aromatic amino acid, an N-alkyl-substituted glycine such as N-butylglycine to replace any nonpolar amino acid (e.g., L, V, I, etc.), and an N-(aminoalkyl)glycine to replace any basic polar amino acid (e.g., K and R).

Where an amino acid sequence is provided herein, L-, D-, or beta amino acid versions of the sequence are also contemplated as well as retro, inversion (inverso), and retro-inversion (retroinverso) isoforms. In addition, conservative substitutions (e.g., in the targeting peptide, and/or antimicrobial peptide, and/or linker peptide (when present)) are contemplated. Non-protein backbones, such as PEG, alkane, ethylene bridged, ester backbones, and other backbones are also contemplated. Also fragments ranging in length from about 5, 6, 7, 8, 9, 10, 11, 12, 13, 14, 15, 16, 17, 18, 19, 20, 21, 22, 23, 24, or 25 amino acid residues up to the full length minus one amino acid of the peptide are contemplated where the fragment retains at least 50%, preferably at least 60% 70% or 80%, more preferably at least 90%, 95%, 98%, 99%, or at least 100% of the activity (e.g., binding specificity and/or avidity, antimicrobial activity, etc.) of the full length peptide are contemplated.

In certain embodiments, conservative substitutions of the amino acid residues comprising any of the sequences described herein are contemplated. In various embodiments one, two, three, four, or five different residues are substituted. The term "conservative substitution" is used to reflect amino acid substitutions that do not substantially alter the activity (e.g., proteolytic inhibition and/or specificity) of the molecule. Typically conservative amino acid substitutions involve substitution one amino acid for another amino acid with similar chemical properties (e.g. charge or hydrophobicity). Certain conservative substitutions include "analog substitutions" where a standard amino acid is replaced by a non-standard (e.g., rare, synthetic, etc.) amino acid differing minimally from the parental residue. Amino acid analogs are considered to be derived synthetically from the standard amino acids without sufficient change to the structure of the parent, are isomers, or are metabolite precursors. Examples of such "analog substitutions" include, but are not limited to, 1) Lys→Orn, 2) Leu→Norleucine, 3) Lys→Lys[TFA], 4) Phe→Phe[Gly], and 5) δ-amino butylglycine→ξ-amino hexylglycine, where Phe[gly] refers to phenylglycine (a Phe derivative with a H rather than $CH_3$ component in the R group), and Lys[TFA] refers to a Lys where a negatively charged ion (e.g., TFA) is attached to the amine R group. Other conservative substitutions include "functional substitutions" where the general chemistries of the two residues are similar, and can be sufficient to mimic or partially recover the function of the native peptide. Strong functional substitutions include, but are not limited to 1) Gly/Ala, 2) Arg/Lys, 3) Ser/Tyr/Thr, 4) Leu/Ile/Val, 5) Asp/Glu, 6) Gln/Asn, and 7) Phe/Trp/Tyr, while other functional substitutions include, but are not limited to 8) Gly/Ala/Pro, 9) Tyr/His, 10) Arg/Lys/His, 11) Ser/Thr/Cys, 12) Leu/Ile/Val/Met, and 13) Met/Lys (special case under hydrophobic conditions). Various "broad conservative substitutions" include substitutions where amino acid residues replace other amino acid residues from the same biochemical or biophysical grouping. This is similarity at a basic level and stems from efforts to classify the original 20 natural amino acids. Such substitutions include 1) nonpolar side chains: Gly/Ala/Val/Leu/Ile/Met/Pro/Phe/Trp, and/or 2) uncharged polar side chains Ser/Thr/Asn/Gln/Tyr/Cys. In certain embodiments broad-level substitutions can also occur as paired substitutions. For example, any hydrophilic neutral pair [Ser, Thr, Gln, Asn, Tyr, Cys]+[Ser, Thr, Gln, Asn, Tyr, Cys] can may be replaced by a charge-neutral charged pair [Arg, Lys, His]+[Asp, Glu]. The following six groups each contain amino acids that, in certain embodiments, are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K), Histidine (H); 5) Isoleucine (I), Leucine (L), Methionine (M), Valine (V); and 6) Phenylalanine (F), Tyrosine (Y), Tryptophan (W). Where amino acid sequences are disclosed herein, amino acid sequences comprising, one or more of the above-identified conservative substitutions are also contemplated.

In certain embodiments, peptides compromising at least 80%, preferably at least 85% or 90%, and more preferably at least 95% or 98% sequence identity with any of the sequences described herein are also contemplated, as are peptoids corresponding to any of these. The terms "identical" or percent "identity," refer to two or more sequences that are the same or have a specified percentage of amino acid residues that are the same, when compared and aligned for maximum correspondence, as measured using one of the following sequence comparison algorithms or by visual inspection. With respect to the peptides described herein, in typical embodiments, sequence identity is determined over the full length of the peptide. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988)

*Proc. Natl. Acad. Sci., USA,* 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

"Treating" or "treatment" of a condition as used herein encompasses preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

The term "consisting essentially of" when used with respect to a peptide described herein indicates that the peptide, or variant, analogue, or derivative thereof possesses an activity and/or specificity that is substantially the same as, or greater than, the referenced peptide. In certain embodiments, "substantially the same" indicates at least 80%, preferably at least 90%, more preferably at least 95%, and most preferably at least 98%, or at least 99%, or at least 100% of the activity and/or specificity of the referenced peptide. The terms "isolated," "purified," or "biologically pure" refer to material that is substantially or essentially free from components that normally accompany it as found in its native state. In the case of a peptide, an isolated (naturally occurring) peptide is typically substantially free of components with which it is associated in the cell, tissue, or organism. The term isolated also indicates that the peptide is not present in a phage display, yeast display, or other peptide library.

Peptides

In certain embodiments, peptides disclosed herein inhibit the proteolytic activity of insulin-degrading enzyme (IDE). In various embodiments, peptides disclosed herein inhibit IDE with an inhibition constant (K) of less than 15, 10, or 5 µM (measured, for example as described in Example 1). The peptides can include one or more L-, D-, or beta-amino acid residues. The peptides can be modified to increase their stability, especially their stability in a biological milieu. A wide variety of modifications for increasing peptide stability are well known; examples include: the inclusion of D- or beta-amino acids, amino acid analogues, or modified linkages in peptides (e.g., as in peptoids), cyclization, addition of terminal protecting groups or of a polymer that increases stability in a biological milieu. Suitable modifications include, but are not limited to, those described herein.

The peptides described herein are useful in methods of improving the appearance and/or texture of skin and/or promoting wound healing, as well as in methods of treating diabetes, and especially for enhancing wound healing in diabetic subjects. Peptides useful in these methods typically inhibit IDE to a sufficient degree that the peptides can be used to, or included in formulations that, produce a therapeutic benefit that is not outweighed by the risk of toxicity or undesirable side-effects. Examples include peptides having $K_i$s of less than 15, 10, or 5 µM. A therapeutic benefit is achieved when at least one symptom of a disease or disorder (e.g., diabetes) is ameliorated and/or an underlying cause of the disease or disorder is reduced, blocked, or reversed, and/or progression of the disease or disorder is slowed. Symptoms of diabetes that are particularly relevant to the present disclosure include slowed or stalled wound healing, persistent or chronic wounds, which, when unresolved, often necessitate amputation.

Peptide Preparation

The peptides described herein can be chemically synthesized using standard chemical peptide synthesis techniques or, particularly where the peptide does not comprise "D" amino acid residues, the peptide can be recombinantly expressed. Where the "D" polypeptides are recombinantly expressed, a host organism (e.g., bacteria, plant, fungal cells, etc.) can be cultured in an environment where one or more of the amino acids is provided to the organism exclusively in a D form. Recombinantly expressed peptides in such a system then incorporate those D-amino acids.

In certain embodiments, D-amino acids can be incorporated in recombinantly expressed peptides using modified amino acyl-tRNA synthetases that recognize D-amino acids.

In certain embodiments the peptides are chemically synthesized by any of a number of fluid or solid-phase peptide synthesis techniques known to those of skill in the art. Solid-phase synthesis in which the C-terminal amino acid of the sequence is attached to an insoluble and/or solid support followed by sequential addition of the remaining amino acids in the sequence is a preferred method for the chemical synthesis of the polypeptides of this invention. Techniques for solid-phase peptide synthesis are well known to those of skill in the art and are described, for example, by Barany and Merrifield (1963) *Solid-Phase Peptide Synthesis*; pp. 3-284 in *The Peptides: Analysis, Synthesis, Biology. Vol. 2: Special Methods in Peptide Synthesis, Part A.*; Merrifield et al. (1963) *J. Am. Chem. Soc.,* 85: 2149-2156, and Stewart et al. (1984) *Solid Phase Peptide Synthesis,* 2nd ed. Pierce Chem. Co., Rockford, Ill.

It is noted that in the chemical synthesis of peptides, particularly peptides comprising D amino acids, the synthesis usually produces a number of truncated peptides in addition to the desired full-length product. Thus, the peptides are typically purified using standard methods well known to those of skill in the art, e.g., high-pressure liquid chromatography (HPLC).

D-amino acids, beta-amino acids, non-natural amino acids, and the like can be incorporated at one or more positions in the peptide simply by using the appropriately derivatized amino acid residue in the chemical synthesis. Modified residues for solid-phase peptide synthesis are commercially available from a number of suppliers (see, e.g., Advanced Chem Tech, Louisville; Nova Biochem, San Diego; Sigma-Aldrich, St Louis; Bachem California Inc., Torrance, etc.). The D-form and/or otherwise modified amino acids can be completely omitted or incorporated at any position in the peptide as desired. Thus, for example, in certain embodiments, the peptide can comprise a single modified acid, while in other embodiments, the peptide comprises at least: 2, 3, 4, 5, 6, 7, 8, 9, 10, 11, or even all modified amino acids. In certain embodiments, every or essentially every amino acid is a D-form amino acid.

However produced, peptides can be purified away from other components using any suitable methods known to one of skill in the art. Substantially pure peptide compositions of at least about 90 to 95% homogeneity are preferred, and 98 to 99% or higher homogeneity are most preferred.

After chemical synthesis, biological expression, or purification, the peptide may possess a conformation substantially different than the desired native conformation. In this case, it may be necessary to denature and reduce the peptide and then to cause the molecule to re-fold into the preferred conformation. Methods of reducing and denaturing proteins and inducing re-folding are well known to those of skill in the art (see, e.g., Debinski et al. (1993) *J. Biol. Chem.,* 268: 14065-14070; Kreitman and Pastan (1993) *Bioconjug. Chem.,* 4: 581-585; and Buchner, et al., (1992) *Anal.*

*Biochem.*, 205: 263-270). Debinski et al., for example, describes the denaturation and reduction of inclusion body proteins in guanidine-DTE. The protein is then refolded in a redox buffer containing oxidized glutathione and L-arginine.

Protecting Groups

While the various peptides described herein may be shown with no protecting groups, in certain embodiments they can bear one, two, three, four, or more protecting groups. In various embodiments, the protecting groups can be coupled to the C- and/or N-terminus of the peptide(s) and/or to one or more internal residues comprising the peptide(s) (e.g., one or more R-groups on the constituent amino acids can be blocked). Thus, for example, in certain embodiments, any of the peptides described herein can bear, e.g., an acetyl group protecting the amino terminus and/or an amide group protecting the carboxyl terminus.

Without being bound by a particular theory, it was discovered that addition of a protecting group, particularly to the C-termini and, in certain embodiments, the N-termini can improve the stability and efficacy of the peptide.

A wide number of protecting groups are suitable for this purpose. Such groups include, but are not limited to acetyl, amide, and alkyl groups with acetyl and alkyl groups often being used for N-terminal protection and amide groups being used for C-terminal protection. In certain embodiments, the protecting groups include, but are not limited to alkyl chains, as in fatty acids, propionyl, formyl, and others. Particularly preferred carboxyl protecting groups include amides, esters, and ether-forming protecting groups. In one embodiment, an acetyl group is used to protect the N-terminus and an amide group is used to protect the C-terminus. Certain particularly preferred blocking groups include alkyl groups of various lengths, e.g., groups having the formula: $CH_3-(CH_2)_n-CO-$ where n ranges from about 0 to about 20, preferably from about 1 to about 16 or 18, more preferably from about 3 to about 13, and most preferably from about 0 to about 10.

In certain embodiments, the acid group on the C-terminal residue can be blocked with an alcohol, aldehyde or ketone group and/or the N-terminal residue can have the natural amide group, or be blocked with an acyl, carboxylic acid, alcohol, aldehyde, or ketone group.

Other protecting groups include, but are not limited to fluorenylmethyloxycarbonyl (Fmoc), 9-fluoreneacetyl group, 1-fluorenecarboxylic group, 9-fluorenecarboxylic group, 9-fluorenone-1-carboxylic group, benzyloxycarbonyl, xanthyl (Xan), trityl (Trt), 4-methyltrityl (Mtt), 4-methoxytrityl (Mmt), 4-methoxy-2,3,6-trimethyl-benzenesulphonyl (Mtr), mesitylene-2-sulphonyl (Mts), 4,4-dimethoxybenzhydryl (Mbh), tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), benzyloxymethyl (Bom), t-butyloxycarbonyl (Tboc), cyclohexyloxy (cHxO), t-butoxymethyl (Bum), t-butoxy (tBuO), t-butyl (tBu), and trifluoroacetyl (TFA).

Protecting/blocking groups are well known to those of skill as are methods of coupling such groups to the appropriate residue(s) comprising the peptides of this invention (see, e.g., Greene et al., (1991) *Protective Groups in Organic Synthesis, 2nd ed.*, John Wiley & Sons, Inc. Somerset, N.J.). In illustrative embodiment, for example, acetylation is accomplished during the synthesis when the peptide is on the resin using acetic anhydride. Amide protection can be achieved by the selection of a proper resin for the synthesis. For example, a rink amide resin can be used. After the completion of the synthesis, the semi-permanent protecting groups on acidic bifunctional amino acids such as Asp and Glu and basic amino acid Lys, hydroxyl of Tyr are all simultaneously removed. The peptides released from such a resin using acidic treatment comes out with the N-terminal residue protected as acetyl and the carboxyl protected as $NH_2$ and with the simultaneous removal of all of the other protecting groups.

Peptide Circularization

In certain embodiments the peptides described herein are circularized/cyclized to produce cyclic peptides. Cyclic peptides, as contemplated herein, include head/tail, head/side chain, tail/side chain, and side chain/side chain cyclized peptides. In addition, peptides contemplated herein include homodetic versions, containing only peptide bonds, and heterodetic versions containing in addition or alternatively disulfide, ester, thioester-bonds, or other bonds.

The cyclic peptides can be prepared using virtually any art-known technique for the preparation of cyclic peptides. For example, the peptides can be prepared in linear or non-cyclized form using conventional solution or solid phase peptide syntheses and cyclized using standard chemistries. Preferably, the chemistry used to cyclize the peptide will be sufficiently mild so as to avoid substantially degrading the peptide. Suitable procedures for synthesizing the peptides described herein as well as suitable chemistries for cyclizing the peptides are well known in the art.

In various embodiments cyclization can be achieved via direct coupling of the N- and C-terminus to form a peptide (or other) bond, but can also occur via the amino acid side chains. Furthermore, cyclization can be based on the use of other functional groups, including but not limited to amino, hydroxy, sulfhydryl, halogen, sulfonyl, carboxy, and thiocarboxy. These groups can be located at the amino acid side chains or be attached to their N- or C-terminus.

Accordingly, it is to be understood that the chemical linkage used to covalently cyclize the peptides of the invention need not be an amide linkage. In many instances, it may be desirable to modify the N- and C-termini of the linear or non-cyclized peptide so as to provide, for example, reactive groups that may be cyclized under mild reaction conditions. Such linkages include, by way of example and not limitation, amide, ester, thioester, $CH_2-NH$, etc. Techniques and reagents for synthesizing peptides having modified termini and chemistries suitable for cyclizing such modified peptides are well-known in the art.

Alternatively, in instances where the ends of the peptide are conformationally or otherwise constrained so as to make cyclization difficult, it may be desirable to attach linkers to the N- and/or C-termini to facilitate peptide cyclization. Of course, it will be appreciated that such linkers will bear reactive groups capable of forming covalent bonds with the termini of the peptide. Suitable linkers and chemistries are well-known in the art and include those previously described.

Cyclic peptides and depsipeptides (heterodetic peptides that include ester (depside) bonds as part of their backbone) have been well characterized and show a wide spectrum of biological activity. The reduction in conformational freedom brought about by cyclization often results in higher binding affinities. Frequently in these cyclic compounds, extra conformational restrictions are also built in, such as the use of D- and N-alkylated-amino acids, $\alpha,\beta$-dehydro amino acids or $\alpha,\alpha$-disubstituted amino acid residues.

Methods of forming disulfide linkages in peptides are well known to those of skill in the art (see, e.g., Eichler and Houghten (1997) *Protein Pept. Lett.* 4: 157-164).

Reference may also be made to Marlowe (1993) *Biorg. Med. Chem. Lett.* 3: 437-44, who describes peptide cyclization on TFA resin using trimethylsilyl (TMSE) ester as an orthogonal protecting group; Pallin and Tam (1995) *J. Chem. Soc. Chem. Comm.* 2021-2022, who describe the cyclization of unprotected peptides in aqueous solution by oxime formation; Algin et al. (1994) *Tetrahedron Lett.* 35: 9633-9636, who disclose solid-phase synthesis of head-to-tail cyclic peptides via lysine side-chain anchoring; Kates et al. (1993) *Tetrahedron Lett.* 34: 1549-1552, who describe the production of head-to-tail cyclic peptides by three-dimensional solid phase strategy; Tumelty et al. (1994) *J. Chem. Soc. Chem. Comm.* 1067-1068, who describe the synthesis of cyclic peptides from an immobilized activated intermediate, where activation of the immobilized peptide is carried out with N-protecting group intact and subsequent removal leading to cyclization; McMurray et al. (1994) *Peptide Res.* 7: 195-206), who disclose head-to-tail cyclization of peptides attached to insoluble supports by means of the side chains of aspartic and glutamic acid; Hruby et al. (1994) *Reactive Polymers* 22: 231-241), who teach an alternate method for cyclizing peptides via solid supports; and Schmidt and Langer (1997) *J. Peptide Res.* 49: 67-73, who disclose a method for synthesizing cyclotetrapeptides and cyclopentapeptides.

These methods of peptide cyclization are illustrative and non-limiting. Using the teachings provided herein, other cyclization methods will be available to one of skill in the art.

Administration and Formulations

In certain embodiments, the peptides described herein are administered, often topically, to a subject to improve the appearance and/or texture of skin and/or to promote wound healing. In certain embodiments, the peptides described herein are administered treat diabetes.

Active agents (e.g., peptides) described herein can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Methods of formulating such derivatives are known to those of skill in the art. For example, the disulfide salts of a number of delivery agents are described in PCT Publication WO 2000/059863, which is incorporated herein by reference. Similarly, acid salts of therapeutic peptides, peptoids, or other mimetics, and can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain acid addition salts of the active agents herein include halide salts, such as may be prepared using hydrochloric or hydrobromic acids.

Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. In certain embodiments, basic salts include alkali metal salts, e.g., the sodium salt, and copper salts.

For the preparation of salt forms of basic drugs, the $pK_a$ of the counterion is preferably at least about 2 pH lower than the $pK_a$ of the drug. Similarly, for the preparation of salt forms of acidic drugs, the $pK_a$ of the counterion is preferably at least about 2 pH higher than the $pK_a$ of the drug. This permits the counterion to bring the solution's pH to a level lower than the $pH_{max}$ to reach the salt plateau, at which the solubility of salt prevails over the solubility of free acid or base. The generalized rule of difference in $pK_a$ units of the ionizable group in the active pharmaceutical ingredient (API) and in the acid or base is meant to make the proton transfer energetically favorable. When the $pK_a$ of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

In various embodiments, preparation of esters typically involves functionalization of hydroxyl and/or carboxyl groups that are present within the molecular structure of the active agent. In certain embodiments, the esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants or prepared from an anhydride or an acid chloride by reaction with ammonia or a lower alkyl amine.

Peptides can be administered locally (e.g., topically) or systemically, depending on the indication. In various embodiments, administration is topical, transdermal, oral, buccal, sublingual, nasal (or otherwise inhaled), rectal, parenteral, etc. The compositions can be administered in a variety of unit dosage forms depending upon the method of administration. Suitable unit dosage forms, include, but are not limited to powders, tablets, pills, capsules, lozenges, pulmonary dosage forms (e.g., pulmonary dosage forms such as solutions for nebulizers, micronized powders for metered-dose inhalers, and the like), suppositories, patches, nasal sprays, injectables, implantable sustained-release formulations, lipid complexes, etc.

The active agents described herein can also be combined with a pharmaceutically acceptable carrier (excipient) to form a pharmacological composition. In certain embodiments, pharmaceutically acceptable carriers include those approved by a regulatory agency of the Federal or a state government or listed in the U.S. Pharmacopeia or other generally recognized pharmacopeia for use in/on animals, and more particularly in/on humans. A "carrier" refers to, for example, a diluent, adjuvant, excipient, auxiliary agent or vehicle with which an active agent of the present invention is administered.

Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, BHT (butylated hydroxytoluene), chelating agents, low molecular weight proteins, protection and uptake enhancers such as lipids, compositions that reduce the clearance or hydrolysis of the active agents, or excipients or other stabilizers and/or buffers.

The active agent(s) can be formulated with other physiologically acceptable compounds, particularly for use in the preparation of tablets, capsules, gel caps, and the like can include, but are not limited to, binders, diluent/fillers, disentegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., active peptide) and the resulting composition is compressed. If desired, the compressed product is coated, e.g., known methods for masking the taste or for enteric dissolution or sustained release. Suitable coating materials include, but are not limited to ethyl-cellulose, hydroxymethylcellulose, polyoxyethylene glycol, cellulose acetate phthalate, hydroxypropylmethylcellulose phthalate, hydroxypropylmethylcellulose acetate succinate, and Eudragit (Evonik, Germany; methacrylic-acrylic copolymers).

Other physiologically acceptable compounds that can be included with the active agent(s) include wetting agents, emulsifying agents, dispersing agents or preservatives that are particularly useful for preventing the growth or action of microorganisms. Various preservatives are well known and include, for example, phenol and sorbic acid. One skilled in the art appreciates that the choice of pharmaceutically acceptable carrier(s), including a physiologically acceptable compound depends, for example, on the route of administration of the active agent(s) and on the particular physiochemical characteristics of the active agent(s).

In certain embodiments, the excipients are sterile and generally free of undesirable matter. These compositions can be sterilized by conventional, well-known sterilization techniques. For various oral dosage form excipients such as tablets and The dosage of active agent(s) can vary widely, and will be selected primarily based on activity of the active ingredient(s), body weight and the like in accordance with the particular mode of administration selected and the patient's needs. In various embodiments dosages can be provided ranging from about 0.1 or 1 mg/kg/day to about 50 mg/kg/day and sometimes higher. Typical dosages range from about 3 mg/kg/day to about 3.5 mg/kg/day, for example, from about 3.5 mg/kg/day to about 7.2 mg/kg/day, from about 7.2 mg/kg/day to about 11.0 mg/kg/day, or from about 11.0 mg/kg/day to about 15.0 mg/kg/day. In certain embodiments, dosages range from about 10 mg/kg/day to about 50 mg/kg/day. In certain embodiments, dosages range from about 20 mg to about 50 mg given orally twice daily. It will be appreciated that such dosages may be varied to optimize a therapeutic and/or prophylactic regimen in a particular subject or group of subjects.

In certain embodiments, the active agents of this invention are administered to the oral cavity. This is readily accomplished by the use of lozenges, aerosol sprays, mouthwash, coated swabs, and the like.

In certain embodiments the active agents of this invention are administered systemically (e.g., orally, or as an injectable) in accordance with standard methods well known to those of skill in the art. In other preferred embodiments, the agents, can also be delivered through the skin using conventional transdermal drug delivery systems, or transdermal drug delivery systems utilizing minimally invasive approaches (e.g., in combination with devices enabling microporation of upper layers of skin). Illustrative transdermal delivery systems include, but are not limited to transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active agent(s)" that is ultimately available for delivery to the surface of the skin. Thus, for example, the "reservoir" may include the active agent(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the patch and provides the device with much of its flexibility. The material selected for the backing layer is preferably substantially impermeable to the active agent(s) and any other materials that are present.

Formulations for topical delivery include, but are not limited to, ointments, gels, sprays, fluids, creams, reconstituted extracellular matrix complexes, synthetic skin, and the like. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Active agents can also be delivered topically using reconstituted extracellular matrix complexes, such as Matrigel® (U.S. Pat. No. 4,829,000, which is incorporated by reference herein for its disclosure of these materials) or synthetic skin-type materials, such as those disclosed in International Pub. Nos. WO2015198002 and WO2013164635 and U.S. Pat. No. 9,514,658 (each of which is incorporated by reference herein for its disclosure of these materials).

In certain embodiments, one or more active agents of the present invention can be provided as a "concentrate", e.g., in a storage container (e.g., in a premeasured volume) ready for dilution, or in a soluble capsule ready for addition to a volume of water, alcohol, hydrogen peroxide, or other diluent.

While the invention is described with respect to use in humans, it is also suitable for animal, e.g., veterinary use. Thus certain preferred organisms include, but are not limited to humans, non-human primates, canines, equines, felines, porcines, ungulates, largomorphs, and the like.

In various embodiments, the peptide(s) is present in the formulation at a concentration ranging from about 1 nM, to about 1, 10, or 100 mM, more preferably from about 1 nM, about 10 nM, about 100 nM, about 1 μM, or about 10 μM to about 50 μM, about 100 μM, about 200 μM, about 300 μM, about 400 μM, or about 500 μM, preferably from about 1 μM, about 10 μM, about 25 μM, or about 50 μM to about 1 mM, about 10 mM, about 20 mM, or about 5 mM, most preferably from about 10 μM, about 20 μM, or about 50 μM to about 100 μM, about 150 μM, or about 200 μM.

Example 1: Peptidic Inhibitors of Insulin-Degrading Enzyme Suitable for Dermatological Applications Discovered Via Phage Display Abstract Insulin-degrading enzyme (IDE) is an atypical Zn-metalloendopeptidase that hydrolyzes insulin and other intermediate-sized peptide hormones implicated in skin health and wound healing. Pharmacological inhibitors of IDE administered internally have been shown to slow the breakdown of insulin and thereby potentiate insulin action. Given the importance of insulin and other IDE substrates for a variety of dermatological processes, pharmacological inhibitors of IDE suitable for topical applications could hold significant therapeutic and cosmetic potential. Existing IDE inhibitors, however, are prohibitively expensive, difficult to synthesize and of undetermined toxicity. Here we used phage display to discover novel peptidic inhibitors of IDE, which were subsequently characterized in vitro and in cell culture assays. Among several peptide sequences tested, a cyclic dodecapeptide dubbed P12-3A was found to potently inhibit the degradation of insulin ($K_i$=2.5±0.31 μM) and other substrates by IDE, while also being resistant to degradation, stable in biological milieu, and highly selective for IDE. In cell culture, P12-3A was shown to potentiate several insulin-induced processes, including the transcription, translation and secretion of alpha-1 type I collagen in primary murine skin fibroblasts, and the migration of keratinocytes in a scratch wound migration assay. By virtue of its potency, stability, specificity for IDE, low cost of synthesis, and demonstrated ability to potentiate insulin-induced processes involved in wound healing and skin health, P12-3A is expected to hold significant therapeutic and cosmetic value for topical applications.

Introduction

Insulin is a pleiotropic peptide hormone that, although best known for its role in blood sugar regulation, is implicated in a wide array of physiological processes relevant to skin health and wound repair (1). Insulin stimulates the proliferation (2,3), differentiation (4) and migration (5,6) of skin fibroblasts and keratinocytes, as well as the production and secretion of extracellular matrix (ECM) proteins, particularly collagen (7-13). Conversely, all of these processes are impaired in the skin of mice with genetic deletion of the insulin receptor (14). Moreover, impairments in wound healing and other skin disorders are common among patients with diabetes (15), a disease characterized by defects in insulin production or action.

Given the importance of insulin signaling to wound healing, topical insulin has been investigated in numerous studies in animals (6,16-20) and humans (21), including several clinical trials (22-24). However, the routine clinical use of topical insulin for wound management is not generally accepted as a first-line treatment, and significant adverse effects—including life-threatening hypoglycemia—have been reported (25).

Our group has been exploring an alternative approach to boosting insulin signaling that obviates the risk of hypoglycemia: namely, pharmacological inhibition of insulin-degrading enzyme (IDE) (26), the principal protease implicated in the catabolism and inactivation of insulin (27). IDE inhibitors have been shown to potentiate insulin action in cultured cells (28) and in vivo (29-31). Recently developed, highly selective IDE inhibitors showed potent antidiabetic properties (29), effects that were attributable to reduced catabolism of insulin. Importantly, mice with genetic deletion of IDE are viable (32-34); thus—unlike insulin—IDE inhibitors possess no intrinsic risk of triggering hypoglycemia. IDE is expressed to high levels in skin (35,36) and—notably—is especially abundant in wound fluid (37,38) where it degrades insulin (37,38). Thus, topical application of IDE inhibitors could enhance insulin signaling in skin.

Although a number of IDE inhibitors have been developed (28, 29, 39-43), existing compounds are not ideal for topical applications due to their high cost of synthesis and undetermined toxicity. To overcome these limitations, we sought here to develop peptidic inhibitors of IDE that, by their intrinsic nature, would be inexpensive to manufacture and highly unlikely to be toxic. To that end, we used phage display to discover cyclic and linear peptide sequences that bind with high affinity to IDE. Among the sequences analyzed, a dodecameric, cyclic peptide dubbed P12-3A, proved to be a potent inhibitor of IDE that was stable in a biologic milieu. P12-3A was found to potentiate a number of insulin-stimulated processes in cultured skin cells, including collagen production in fibroblasts and migration of keratinocytes in a scratch wound assay. Given its high potency, selectivity for IDE, minimal potential for toxicity, and its low cost of manufacture, P12-3A represents an ideal IDE inhibitor for topical use with significant therapeutic and cosmetic potential.

Results

Figure 5A:
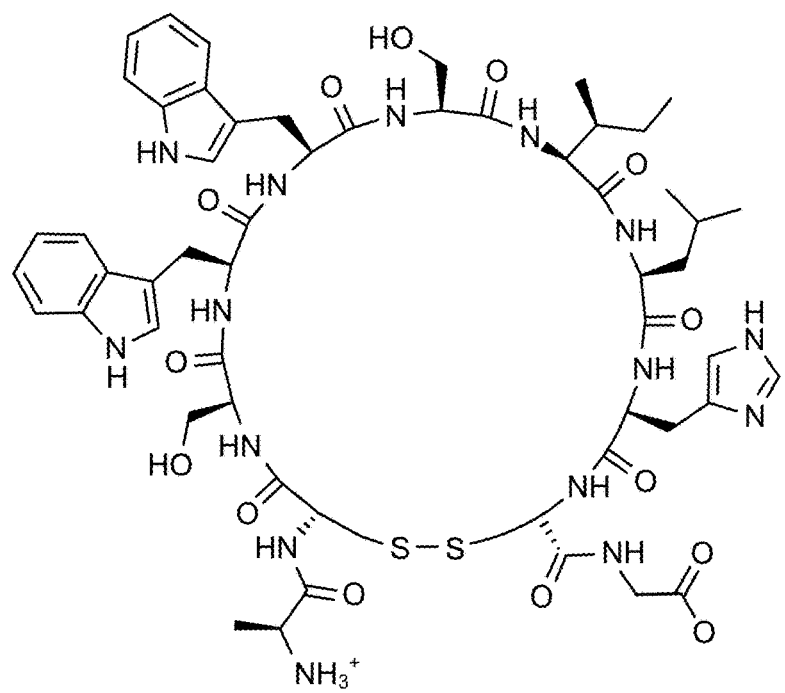
FIG. 5A-F. Structures of parent peptides discovered by phage display. Note that P12-3, although derived from a library of primarily linear peptides, is predicted to be a cyclic peptide.
Figure 5B:
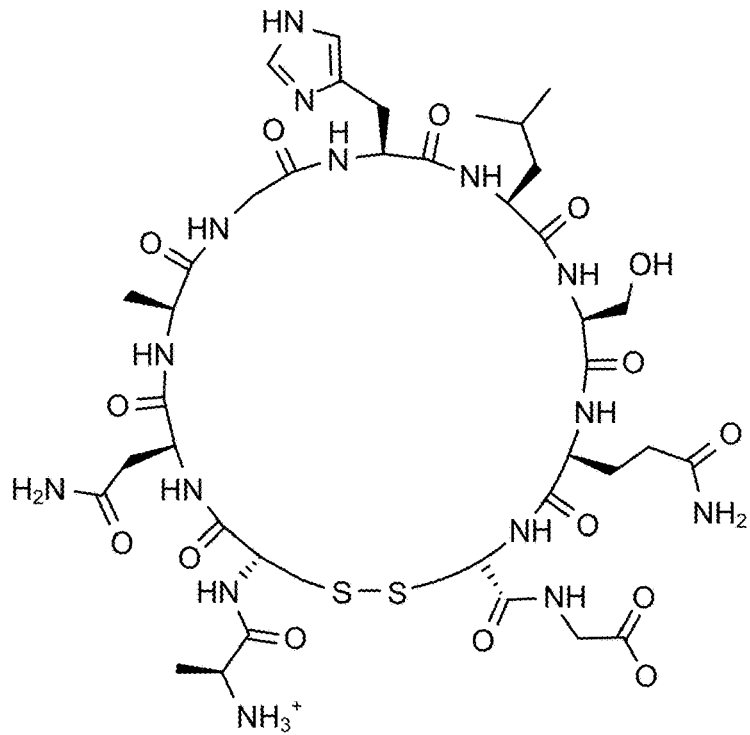
Figure 5C:
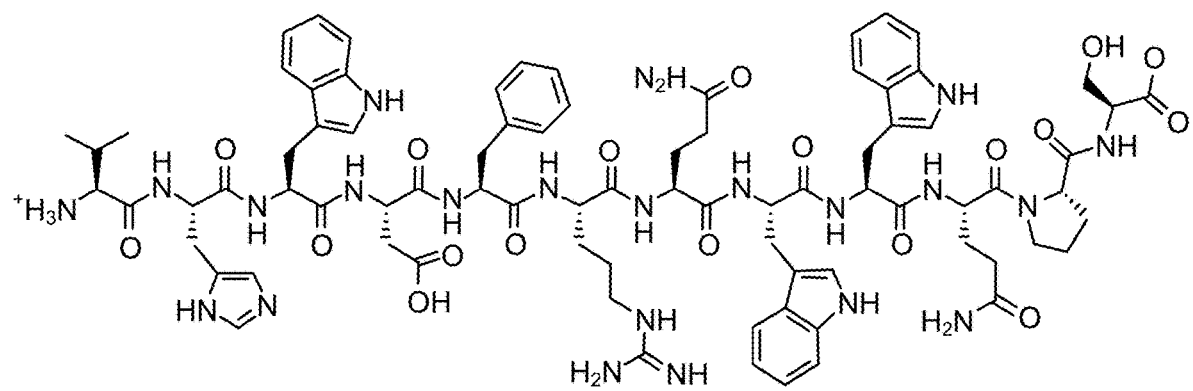
Figure 5D:
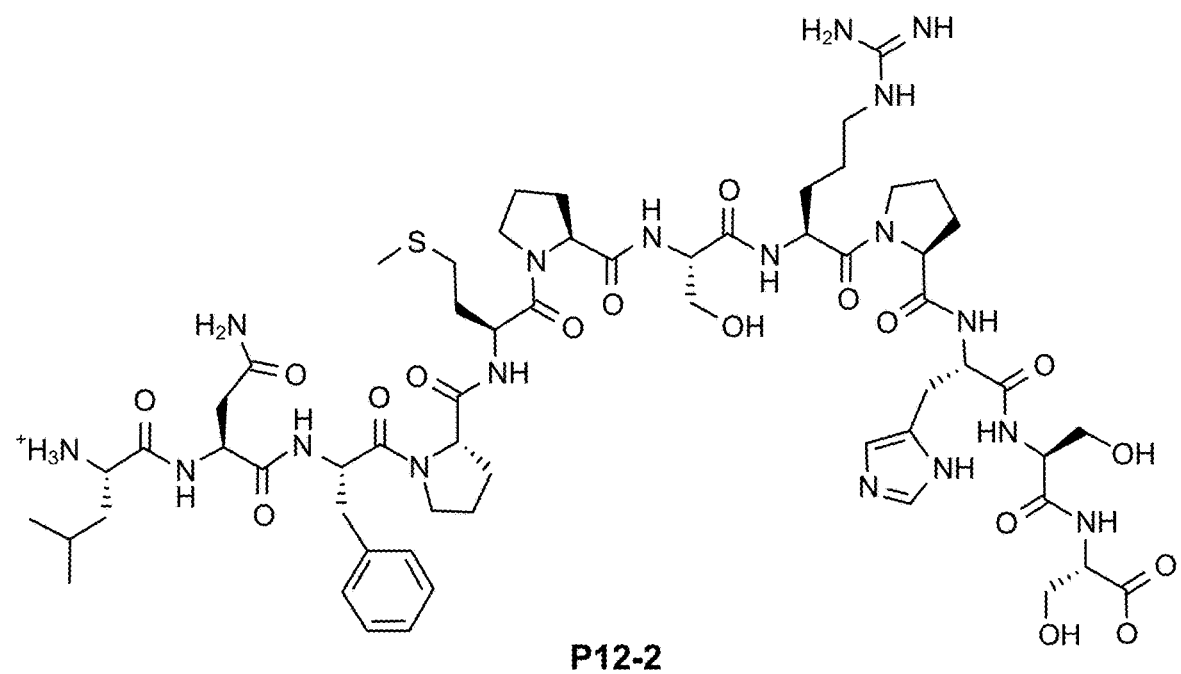

To identify novel peptidic inhibitors of IDE, we utilized phage display technology (44) to select for sequences that bind with high affinity to immobilized recombinant human IDE, using two phage libraries. Reasoning that IDE possesses an intrinsic affinity for cyclic peptides, we screened a library of cyclic peptides (Ph.D.™-C7C, New England Biolabs) comprised of essentially all combinations of 7 natural amino acids flanked by two cysteines (ACXXXXXXXCGGG . . . [SEQ ID NO:52]), where X represents any amino acid). The two cysteines form a disulfide bond that cyclizes each peptide, the alanine serves to protect the N-terminal cysteine from off-target interactions, and the three glycines form a flexible linker with the bacteriophage coat protein. Three rounds of panning were conducted using immobilized recombinant human IDE, with elution performed by addition of excess insulin in order to selectively identify sequences that bind to the internal chamber of IDE. Twenty clones were selected for DNA sequencing, yielding sixteen unique amino acid sequences (FIG. 1A). From analysis of all sequences (FIG. 1B), a clear consensus sequence emerged (ACSWWSIHLCGGG . . . [SEQ ID NO:53]). This sequence, dubbed C7C-1 (FIG. 1C, FIG. 5A), was selected for subsequent synthesis and testing, together with another that appeared two times (ACNAGHLSQCGGG . . . [SEQ ID NO:54]), dubbed C7C-2 (FIG. 1C, FIG. 5B).

A second library of dodecapeptides (Ph.D.™-12, New England Biolabs), consisting of ~$10^9$ possible combinations of twelve amino acids, was also screened, in this case two separate times, yielding the sequences in FIGS. 1D and 1E. In this case, four sequences appeared multiple times (dubbed 12-1, 12-2, 12-3 and 12-4), and these dodecapeptides were selected for subsequent synthesis and testing (FIG. 1F, FIG. 5C-F).

The six selected peptide sequences (C7C-1, C7C-2, 12-1, 12-2, 12-3 and 12-4) were synthesized, together with a variety of modifications, including N-terminal acetylation, C-terminal amidation and/or truncation at one or both termini, yielding a total of 25 peptides (Table 1).

TABLE 1

Peptide sequences synthesized and their potency in activity assays with FRET1 and insulin.

| Name | N-term | Sequence | C-term | $K_{i\ FRET1}$ (μM) | $K_{i\ Insulin}$ (μM) |
|---|---|---|---|---|---|
| C7C-1 | $NH_3^+$ | ACSWWSIHLCG | $COO^-$ | 112 ± 6 | 3.7 ± 0.7 |
| C7C-1A | $NH_3^+$ | ACSWWSIHLCG | amide | >100 | >10 |
| C7C-1B | $NH_3^+$ | ACSWWSIHLCGGG | $COO^-$ | >100 | >10 |
| C7C-2 | $NH_3^+$ | ACNAGHLSQCG | $COO^-$ | >500 | >10 |
| C7C-2A | $NH_3^+$ | ACNAGHLSQCG | amide | >500 | >10 |
| P12-1 | $NH_3^+$ | VHWDFRQWWQPS | $COO^-$ | 7.7 ± 0.7 | 0.8 ± 0.04 |
| P12-1A | $NH_3^+$ | VHWDFRQWWQPS | amide | 5.0 ± 0.3 | 1.3 ± 0.2 |
| P12-1B | $NH_3^+$ | VHWDFRQW | amide | 41 ± 6.4 | 7.0 ± 1.7 |
| P12-1C | acetyl | FRQWWQPS | $COO^-$ | 139 ± 21 | >10 |
| P12-1D | acetyl | WDFRQWWQ | amide | 140 ± 28 | >10 |
| P12-2 | $NH_3^+$ | LNFPMPSRPHSS | $COO^-$ | >100 | >10 |
| P12-2A | $NH_3^+$ | LNFPMPSRPHSS | amide | >100 | >10 |
| P12-2B | $NH_3^+$ | LNFPMPSR | amide | >500 | >10 |
| P12-2C | acetyl | MPSRPHSS | $COO^-$ | >500 | >10 |
| P12-2D | acetyl | FPMPSRPH | amide | >500 | >10 |
| P12-3 | $NH_3^+$ | QSLPWCYPHCVT | $COO^-$ | 8.9 ± 0.3 | 3.9 ± 1.6 |
| P12-3A | $NH_3^+$ | QSLPWCYPHCVT | amide | 10 ± 0.4 | 4.1 ± 0.3 |
| P12-3B | $NH_3^+$ | QSLPWCYP | amide | 39 ± 20 | >10 |
| P12-3C | acetyl | WCYPHCVT | $COO^-$ | 35 ± 4.7 | >10 |
| P12-3D | acetyl | LPWCTPHC | amide | 102 ± 14 | >10 |
| P12-4 | $NH_3^+$ | WSPISGKFFQRF | $COO^-$ | 3.9 ± 0.5 | 1.5 ± 0.3 |
| P12-4A | $NH_3^+$ | WSPISGKFFQRF | amide | 4.2 ± 1.3 | 2.6 ± 0.7 |
| P12-4B | $NH_3^+$ | WSPISGKF | amide | >500 | >10 |

TABLE 1-continued

Peptide sequences synthesized and their potency in activity assays with FRET1 and insulin.

| Name | N-term | Sequence | C-term | $K_{i\ FRET1}$ (μM) | $K_{i\ Insulin}$ (μM) |
|---|---|---|---|---|---|
| P12-4C | acetyl | SGKFFQRF | COO⁻ | >500 | >10 |
| P12-4D | acetyl | PISGKFFQ | amide | >500 | >10 |

To assess the extent to which these peptide sequences inhibit IDE, we quantified their potency in protease activity assays using recombinant human IDE and two different substrates: FRET1, a fluorogenic peptide (45), and recombinant human insulin. Peptides were initially tested at a few concentrations (10 μM, 100 μM and/or 500 μM) then, for those peptides showing good potency, dose-response relationships were obtained to quantify $IC_{50}$ values, which were subsequently converted to inhibitory constants ($K_i$ values) with the Cheng-Prusoff equation (46).

Among the cyclic peptides tested, C7C-1 exhibited a modest $K_1$ value of 112±6 M against FRET1 but yielded considerably improved potency against insulin ($K_i$=3.7±0.7 μM) (Table 1). None of the other C7C-1 derivatives exhibited $K_i$ values below 100 μM for FRET1 or 10 μM for insulin, nor did C7C-2 or its amidated derivative (Table 1).

Relative to the cyclic peptides C7C-1 and C7C-2 and their derivatives, the unmodified linear peptide P12-1 exhibited significantly lower $K_i$ values against FRET1 (7.7±0.7 μM) as well as insulin (0.8±0.04 μM) (Table 1). The C-terminally amidated version of P12-1, P12-1A, exhibited comparable $K_i$ values against FRET1 and insulin (5.0±0.3 μM and 1.3±0.2 μM, respectively) (Table 1). Among three different 8-amino acid truncated versions of P12-1, the C-terminally truncated variant (P12-1B) exhibited slightly poorer $K_i$ values (41±6.4 μM and 7.0±1.7 μM for FRET1 and insulin, respectively), while the other N-terminally truncated (P12-1C) and N- and C-terminally truncated (P12-1D) variants exhibited relatively poor potency, with $K_i$ values >100 μM for FRET1 and >10 μM for insulin (Table 1). These results suggest the N-terminal residues of P12-1 (VHWD . . . ) are the most critical determinants of its potency.

The dodecapeptide P12-2 contains 3 proline residues (Table 1), which constrain the flexibility of the peptide backbone (FIG. 5D) and, generally speaking, tend to render peptides less vulnerable to proteolytic degradation. However, P12-2 and all its variants exhibited $K_i$ values >100 μM for FRET1 and >10 μM for insulin (Table 1) and were not characterized further.

Figure 3A:
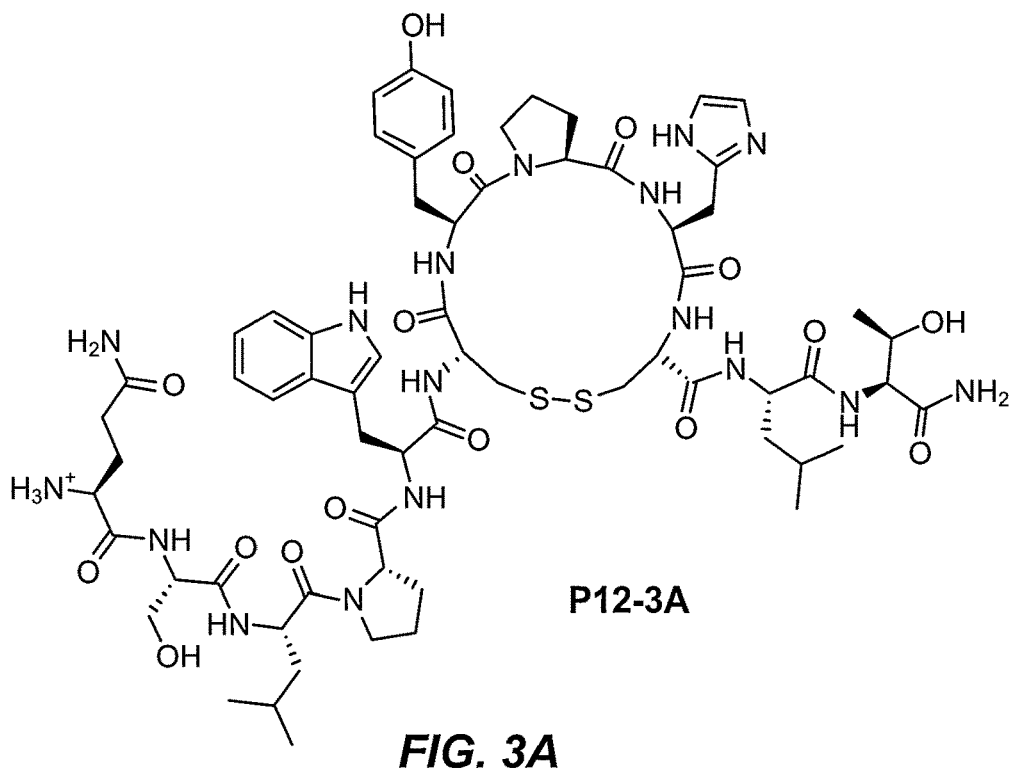
FIG. 3A-B. Structure and activity of P12-3A. A, Structure of cyclized P12-3A. B, Dose-response of P12-3A against insulin degradation by IDE. Data are mean±SEM of 6 independent experiments.
Figure 5E:
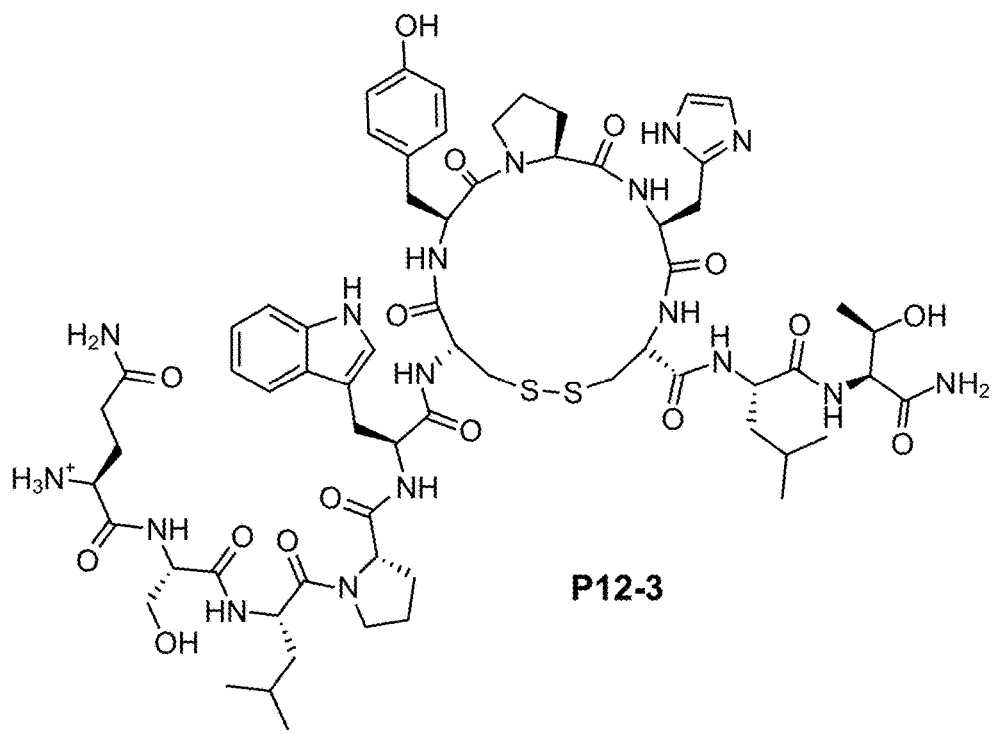
Figure 5F:
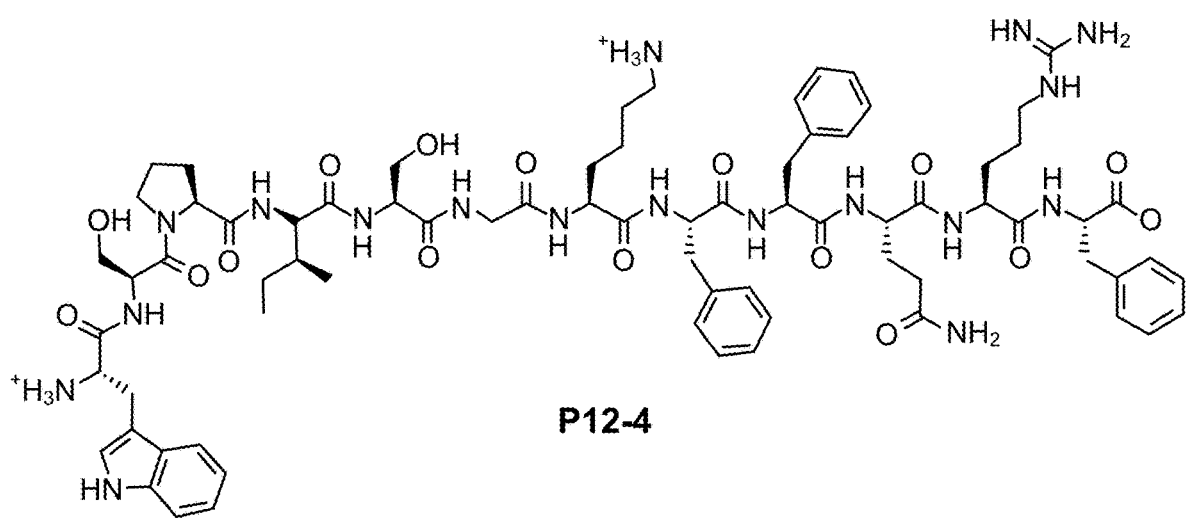

Peptide P12-3 is noteworthy for containing two cysteine residues (Table 1), which are predicted to form a disulfide bond that cyclizes the peptide, together with 2 proline residues (FIG. 5E). The unmodified peptide, P12-3, and its C-terminally amidated variant, P12-3A (FIG. 3A), both showed good potency against FRET1=8.9±0.3 μM and 10±0.4 μM, respectively) and insulin ($K_i$=3.9±1.6 μM and 4.1±0.3 μM, respectively) (Table 1). For the FRET1 substrate, the 8-amino acid truncated variants exhibited poorer potency, with the C-terminally (P12-3B) and N-terminally (P12-3C) truncated variants exhibiting of $K_i$ values of 39±20 μM and 35±4.7 μM, respectively, and the dual N- and C-terminally truncated variant (P12-3D) exhibiting even poorer $K_i$ values of 102±14 μM (Table 1). When insulin was used as a substrate, none of the truncated variants of P12-3 exhibited $K_i$ values <10 μM.

For the final peptide series, P12-4 and its derivatives (Table 5, FIG. 6F), the full-length unmodified (P12-4) and amidated (P12-4A) versions showed good potency against FRET1 ($K_i$=3.9±0.5 μM and 4.2±1.3 μM, respectively) and insulin ($K_i$=1.5±0.3 μM and 2.6±0.7 μM, respectively), while none of the truncated variants (P12-4B, P12-4C and P12-4C) exhibited $K_i$ values below 500 μM or 10 μM for FRET1 or insulin, respectively (Table 1).

Figure 3B:
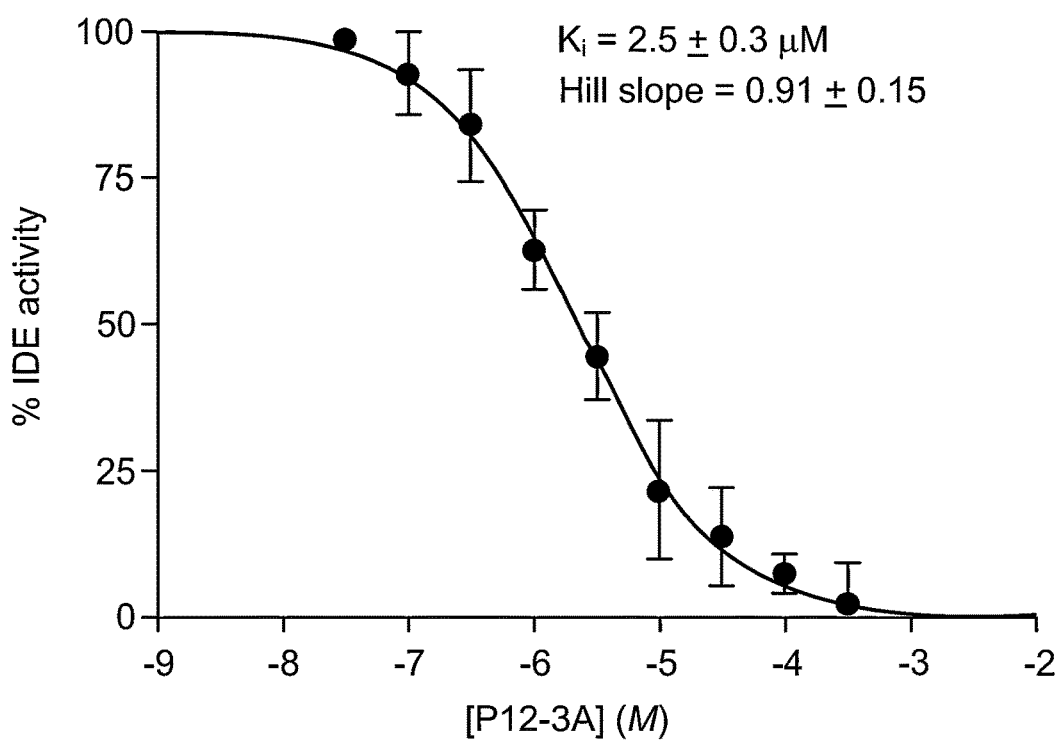
Figure 8A:
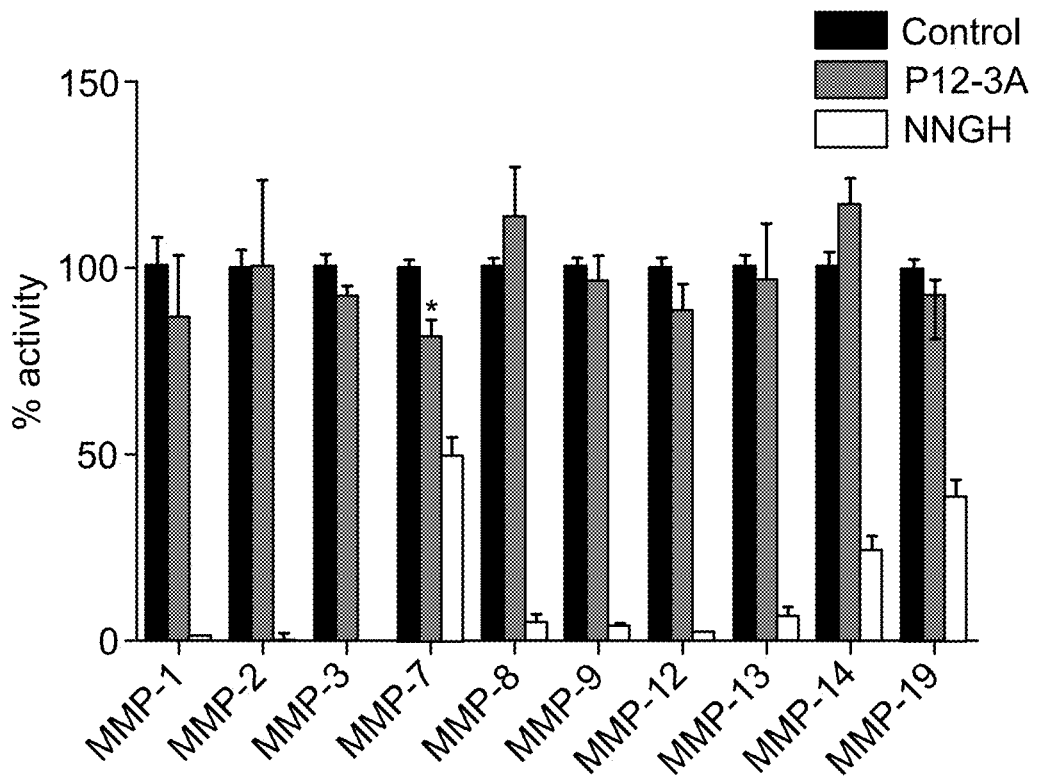
FIG. 8A-B. Selectivity of P12-3A for IDE vis-à-vis other proteases. Activity of P12-3A (100 µM) against (A) multiple matrix-metalloproteases (MMPs) and (B) multiple peptidases of different protease classes. Note that significant inhibition was observed exclusively for IDE, with modest inhibition (~18%) observed for just one of 15 other proteases tested (MMP-7). Data are mean±SEM, n=8-16 per group. P<0.05 by 2-tailed Student's t-test. Note that all positive controls (NNGH or protease inhibitor cocktail (PIC)) exhibited significant inhibition (P<0.01) (not shown for clarity). See Experimental Procedures for details. NEP, neprilysin; mCatD, murine cathepsin D; hCatD, human cathepsin D.
Figure 8B:
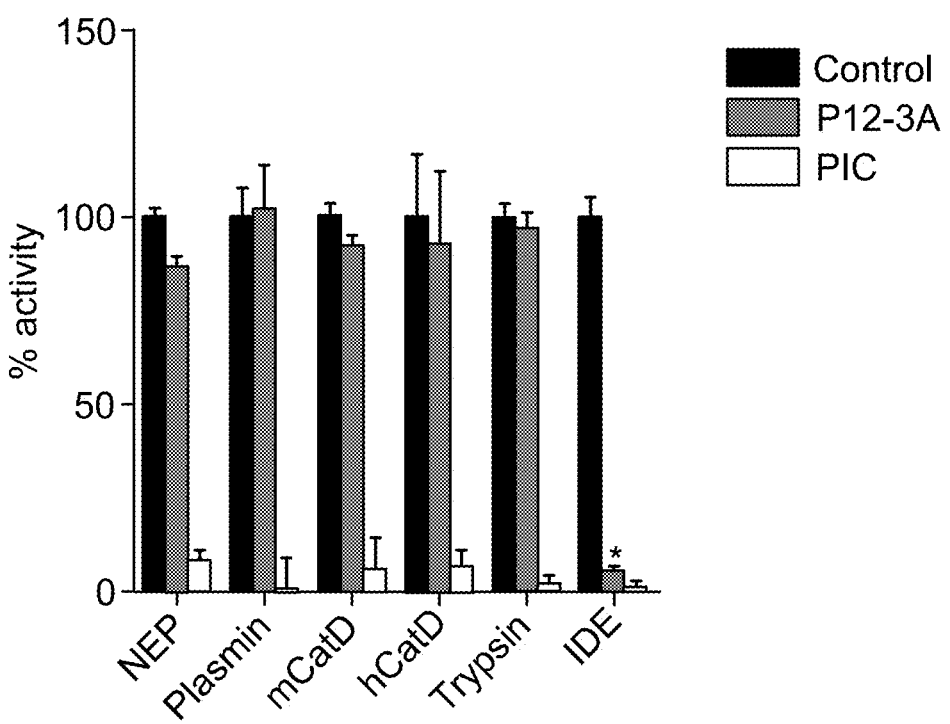

Because IDE is a peptidase, it was critical to determine whether the peptides were degraded by IDE over time. To establish this, we incubated twelve peptides showing quantifiable inhibitory potency together with IDE for an extended period (4 h), then the potency of each was determined and compared to the potency immediately after addition of the enzyme (0 h). As shown in FIG. 2, most peptides exhibited significant reductions in potency (i.e., increases in $K_i$ values) after a 4-h incubation with IDE, likely reflecting proteolytic degradation by IDE. Notable exceptions to this trend included members of the P12-3 family of peptides, particularly P12-3A (QSLPWCYPHCVT-amide), which actually showed a 1-fold increase in potency at the 4-h time point relative to t=0. Because this peptide is capable of forming a disulfide bond between its two cysteines, but was not deliberately cyclized prior to testing, we suspect that the peptide (and related variants) may have cyclized over time, contributing to its stability. Regardless of the precise mechanism underlying its unique stability, taken together with the potency of all peptides against insulin (Table 1), we concluded that P12-3A represented the ideal inhibitor for further studies, and a deliberately cyclized version (FIG. 3A) was therefore synthesized. The highly pure, cosmetic-grade version of P12-3A was confirmed to exhibit similar potency against insulin degradation ($K_i$=2.5±0.31 μM, n=6) (FIG. 3B), and highly consistent inhibition constants were also observed for the degradation of two other substrates, FRET1 ($K_i$=2.7±0.50 μM, n=6) and amyloid β-protein (AB) ($K_i$=2.1±0.34 μM, n=6). P12-3A exhibited essentially no inhibition against 15 different proteases tested (FIG. 8), suggesting it is highly selective for IDE. Based on its potency, stability and selectivity for IDE, P12-3A was selected for use in downstream assays.

Figure 4A:
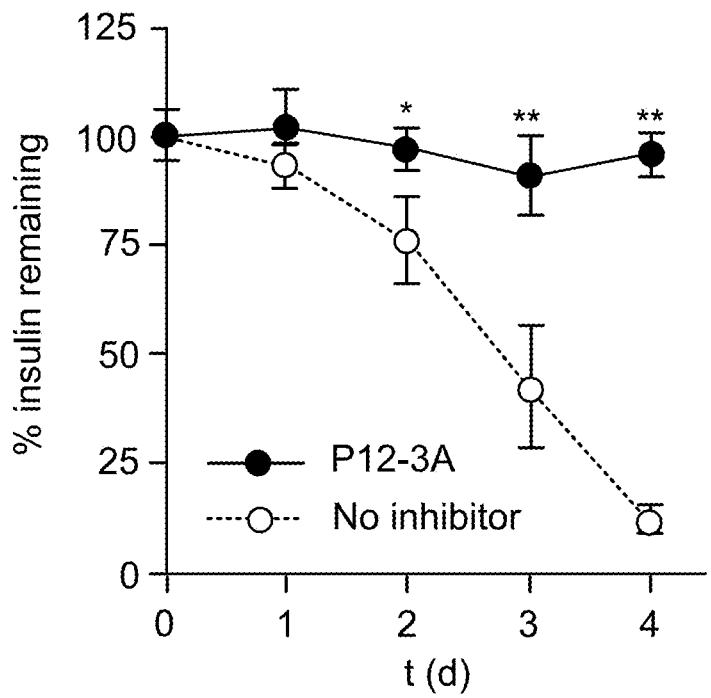
FIG. 4A-F. Effects of P12-3A on cultured skin cells. A, Insulin concentrations as a function of time in logarithmically growing primary murine skin fibroblasts in the absence or presence of P12-3A (100 µM). Note that insulin levels remain constant in the presence of P12-3A, reflecting both the effectiveness of the peptide inhibiting insulin degradation and also the stability of the peptide in biological milieu. Data are mean±SEM of 4 independent replications. *P<0.05, **P<0.01. B, Proliferation of cells in the absence or presence of P12-3A (100 µM). No significant differences were observed. C,D,E, P12-3A (100 µM) potentiates insulin-induced collagen production in skin fibroblasts. Collagen production was assessed by COL1A1 mRNA levels (C), levels of hydroxyproline secreted into the medium (D), and cell-associated mature alpha-1 type I collagen levels detected by Western blotting (E). Data are mean±SEM of 4 independent replications. *P<0.05, **P<0.01. F, P12-3A (100 µM) potentiates the migration of keratinocytes in a scratch wound assay. Migration of HaCaT cells 48 h after induction of a scratch wound in the presence of the indicated quantities of insulin and/or P12-3A (100 µM). Data are mean±SEM of 6 independent replications. *P<0.05, **P<0.01.
Figure 4B:
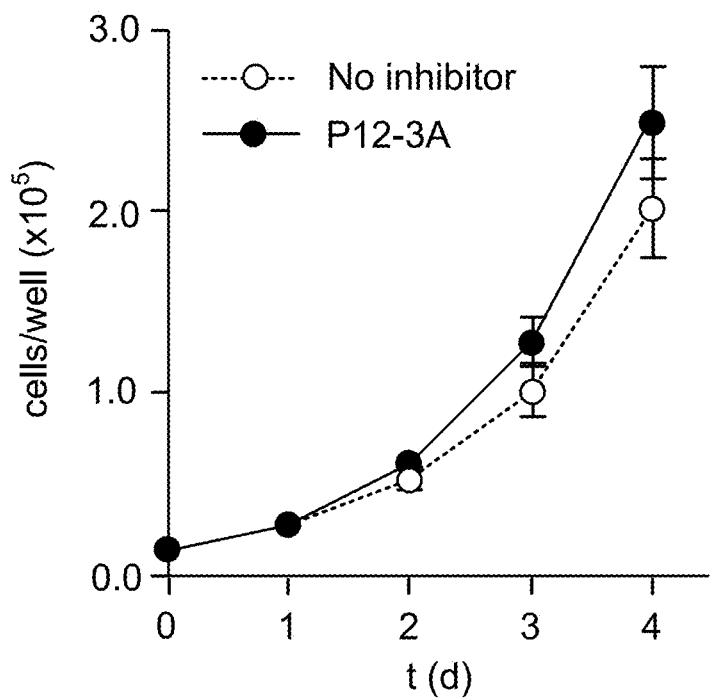
Figure 4C:
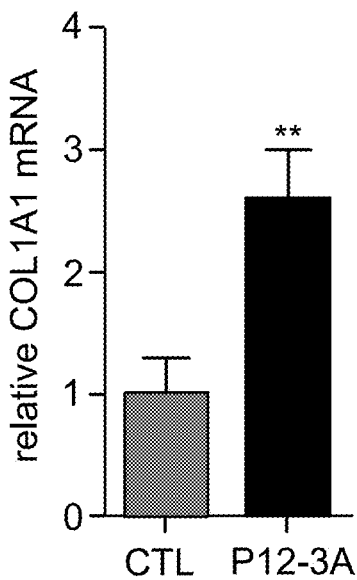
Figure 4D:
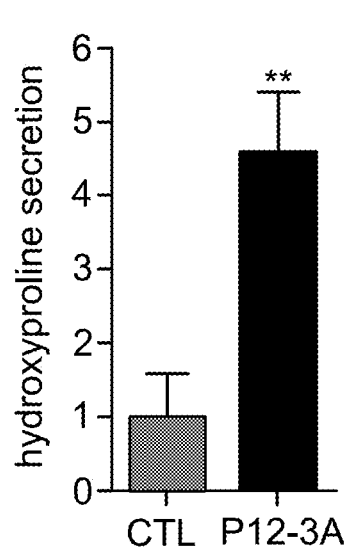
Figure 4E:
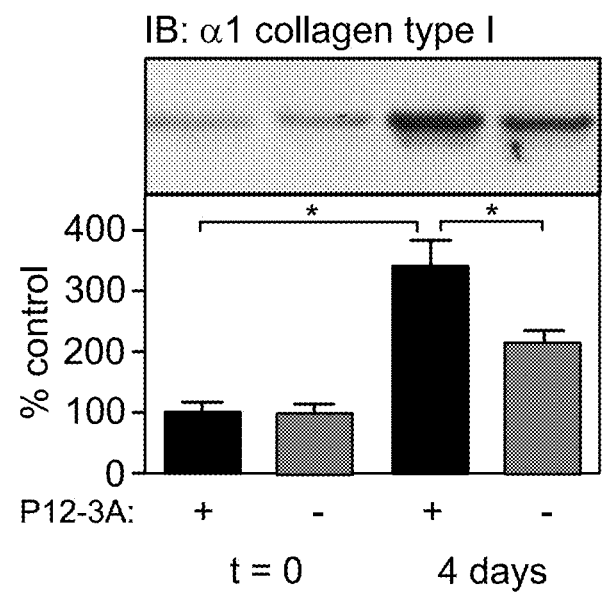
Figure 4F:
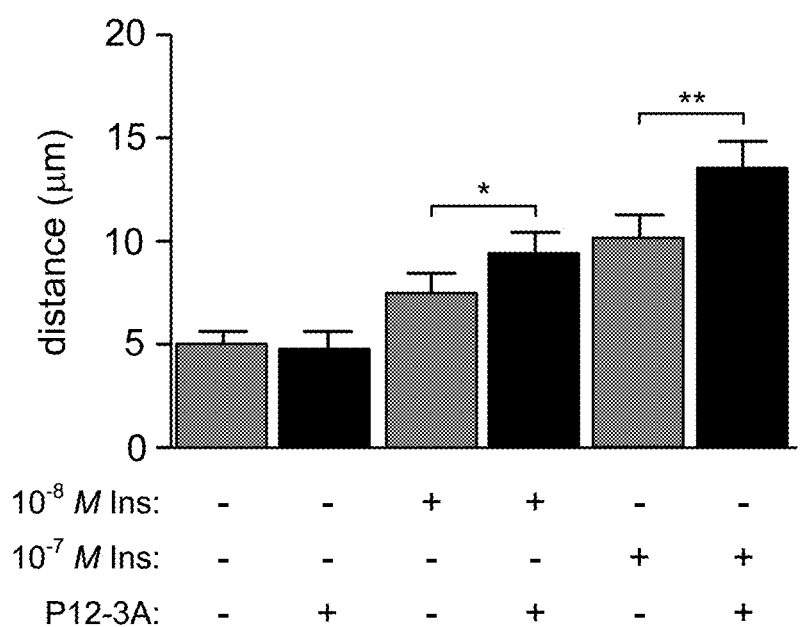

Insulin promotes wound healing and overall skin health by affecting a number of processes, including cell proliferation (2,3), cell migration (5,6), and the production and secretion of ECM components, particularly type I collagen (7-13). We therefore assessed the ability of P12-3A to influence these processes in cultured skin fibroblasts and keratinocytes. To that end, primary mouse skin fibroblasts were grown for 4 d in multiple concentrations of insulin in the presence or absence of P12-3A, and insulin concentration over time was monitored by ELISA. In untreated cells, 10 nM insulin was degraded approximately 90% by day 4 in logarithmically growing cells, whereas insulin levels remained constant in cells treated with 100 μM P12-3A (FIG. 4A). These results demonstrate that P12-3A is effective at inhibiting insulin degradation by skin fibroblasts and, moreover, confirm that the compound is stable in a biological milieu. Relative to control cells, cell proliferation in the presence of 10 nM insulin was found to be modestly increased in the presence of 100 μM P12-3A (FIG. 4B), but this did not achieve statistical significance. Finally, the effects of P12-3A on collagen production in were assessed at both the transcriptional and the posttranslational level in confluent monolayers of fibroblasts. After 4 d of treatment with P12-3A (100 μM), mRNA levels for the major form of collagen, alpha-1 type I collagen (COL1A1), were quantified by RT-PCR and found to be increased to ~2.6 times the levels of untreated cells (FIG. 4C). To assess overall levels of collagen production and secretion, we quantified levels of hydroxyproline, a modified amino acid present almost exclusively in collagen proteins (47). In the presence of P12-3A, hydroxyproline levels secreted into the medium were found to be increased to levels ~4.6 times that secreted by untreated cells (FIG. 4D). Western blotting also confirmed that mature, cell-associated collagen levels were increased in the presence of P12-3A (FIG. 4E). Finally, using an in vitro scratch wound assay, P12-3A was found to significantly increase the migration of keratinocytes in the presence of different concentrations of insulin (FIG. 4F).

Discussion

Although a variety of potent and selective IDE inhibitors have been developed (28, 29, 39-43), current inhibitors are difficult to synthesize and thus expensive to generate and/or contain chemical moieties or constituents with established or undetermined potential for toxicity. Due to these and other considerations, existing IDE inhibitors are poorly suited for topical applications. To overcome these limitations, in the present study we aimed to develop peptidic inhibitors of IDE suitable for use in wound healing or cosmetic applications. Peptides are easy to manufacture and therefore inexpensive to scale up and, to the extent they are composed solely of all-natural amino acids, are unlikely to possess any degree of toxicity. To that end, we used phage display technology to select for a range of peptides that bind to IDE with strong affinity, which were then screened for resistance to degradation by IDE. One cyclic dodecapeptide in particular, P12-3A, proved to be a potent and stable inhibitor of IDE. In cell culture experiments, P12-3A was found to potentiate a number of insulin-stimulated processes relevant to wound healing and skin health, including collagen production by fibroblasts and migration of keratinocytes in response to scratch wounds.

Phage display proved to be a highly effective approach for developing peptidic inhibitors. From among six parent peptides selected for further testing, four exhibited low-micromolar $K_i$ values against insulin, and one (P12-1) exhibited sub-micromolar potency ($K_i$=0.8±0.04 μM). Among the modified versions of these parent peptides, an additional five exhibited $K_i$ values <10 μM; thus nine of the twenty-five peptides tested (36%) showed good activity. These hit rates are markedly higher than those obtained through high-throughput compound screening (41, 45, 48) or other approaches (29). Notably, the potency of P12-1 ($K_i$=800 nM) compares quite favorably to that of the highly optimized and extensively characterized macrocyclic IDE inhibitor, 6 bK, which shows a $K_i$ value of ~100 nM against insulin (29). Given that 6 bK underwent considerable optimization (29), this is an impressive result for a simple, unmodified dodecapeptide.

Although the majority of peptides showed good affinity for IDE, most were also degraded by it. Due to the peculiarities of its structure (26,49-51), IDE is a pure peptidase that cannot degrade proteins; it is therefore unsurprising that phage display would reveal sequences that bind strongly while attached to the bacteriophage coat protein but are nevertheless degraded when synthesized as a short peptide. The particular stability of P12-3A (and related peptides) likely derives from the fact that it contains two cysteines and can therefore form a cyclic peptide. Of note, it is unusual for cyclic peptides to emerge from a library of linear peptides, because cyclization tends to slow the maturation of the bacteriophage, leaving the phage expressing them at a competitive disadvantage when grown in parallel with phage expressing linear peptides. This suggests this peptide sequence was strongly favored during the selection process.

Given its ability to potentiate insulin-stimulated collagen production and cell migration, P12-3A and related peptides would appear hold significant therapeutic potential in wound healing, particularly for diabetic patients (1). Given the accruing evidence that insulin signaling pathways are critical for wound healing (1,22) and, given that IDE is abundant in wound fluid (37,38), where it actively degrades insulin, there is a prediction that pharmacological inhibition of IDE will promote wound healing (28). This prediction is supported by the finding that IDE inhibitors potentiate insulin action in vivo in part by preserving endogenous insulin (32,33) and possibly via actions downstream of insulin receptor binding (28). Importantly, by contrast to direct topical administration insulin, which can cause life-threatening hypoglycemia (25), pharmacological inhibition of IDE possesses no intrinsic risk of triggering hypoglycemia (32-34).

One of the most immediately implementable cosmetic applications for P12-3A may be as an adjuvant for microneedling procedures (52). Also known as percutaneous collagen induction (53,54), microneedling is a minimally invasive, widely used technique by which production of ECM proteins in the dermis can be stimulated essentially by introducing uniform, sterile wounds in a controlled manner (52). Although originally developed for skin rejuvenation, this technique is now being used as a novel treatment for a wide range of cosmetic and medical conditions, including acne, alopecia, stretch marks, hyperhidrosis and scarring of multiple types (52,53). Topical application of P12-3A prior to microneedling would permit the delivery of the peptide subcutaneously (52), thus maximizing its impact on the processes involved in wound repair.

In sum, using phage display technology, we have generated novel peptidic inhibitors of IDE that, by virtue of their low cost of synthesis and minimal risk of toxicity, are suitable for topical applications. Given the importance of insulin in wound healing and normal skin health, these novel inhibitors, as well as future derivatives thereof, will be useful for exploring the involvement of IDE in these processes, and may also hold significant value as adjuvants for medicinal and cosmetic treatments.

Experimental Procedures

Materials—Anti-alpha-1 type I collagen antibody (Cat. No. AB765P) and horseradish peroxidase (HRP)-conjugated anti-rabbit IgG antibody (Cat. No. A0545) were from Sigma-Aldrich (St. Louis, Mo., USA). Anti-glyceraldehyde-3-phosphate dehydrogenase (GAPDH; Cat. No. AF5718) antibody was from R&D Systems (Minneapolis, Minn., USA). HRP-conjugated anti-goat IgG antibody (Cat. No. sc-2354) was from Santa Cruz Biotechnology (Santa Cruz, Calif., USA). Materials for Western blotting and cell culture were from Thermo Fisher Scientific (Waltham, Mass., USA). Insulin ELISAs (Cat. No. 90082) were from Crystal Chem (Downers Grove, Ill., USA). Primary murine skin fibroblasts were a generous gift from Dr. Jorge Busciglio (UC Irvine). HaCaT cells and optimized growth medium were purchased from AddexBio Technologies (San Diego, Calif., USA). Unless specified, all other reagents were from Sigma-Aldrich (St. Louis, Mo., USA).

Phage Display—The selection of IDE-binding peptide sequences was conducted by phage display using the Ph.D.™-C7C and Ph.D.™-12 Phage Display Library Kits from New England Biolabs (Ipswich, Mass., USA) according to manufacturer's recommendations. Briefly, purified, glycerol-free, recombinant human IDE (100 µg/mL) (35) was immobilized onto Corning® High Bind, 96-well, round-bottom plates (Cat. No. CLS3366). After washing and prior to addition of bacteriophage, activity assays with FRET1 (see below) were used to confirm the presence of proteolytically active IDE in wells coated in parallel with those used for panning. Three rounds of panning were conducted, with $2 \times 10^{11}$ phage/well added at each step. After incubation at room temperature for 60 min, bound phage were eluted by addition of excess recombinant human insulin (100 µg/mL) and amplified for the subsequent round of panning. After the third round of panning, the eluate was titered and individual clones were selected for DNA sequencing. Peptide sequences were decoded and consensus sequences searched for using CLC Sequence Viewer (Version 7.5).

Figure 6:
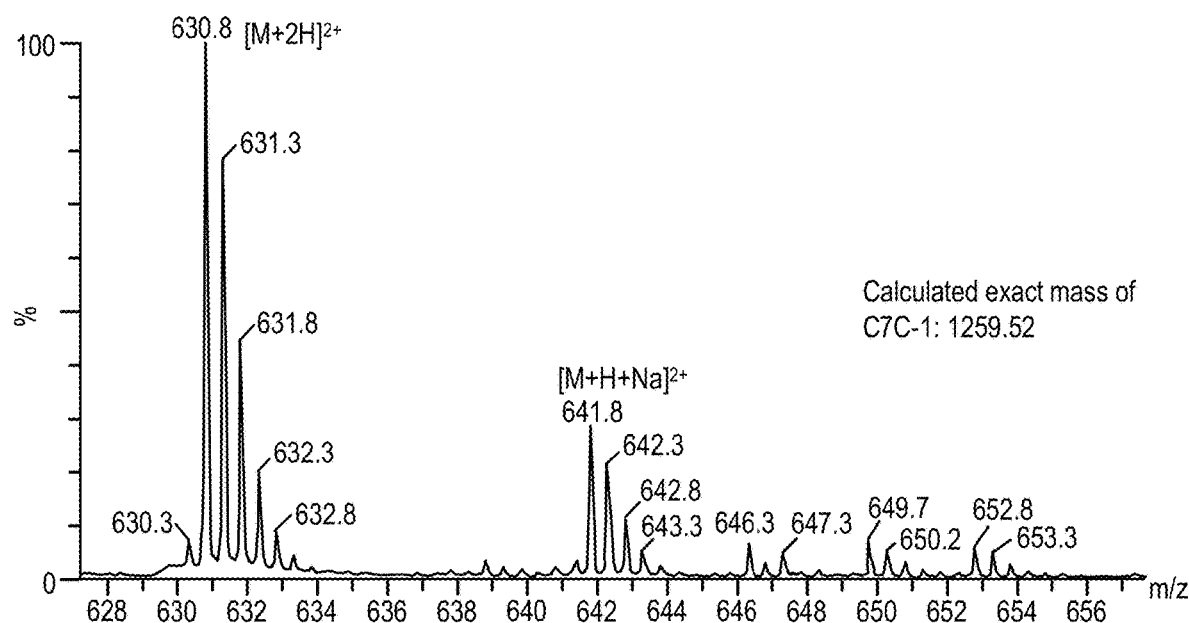
FIG. 6. Confirmation of mass of C7C-1 by ESI-MS. The entire spectrum as well as expanded regions are shown.
Figure 7:
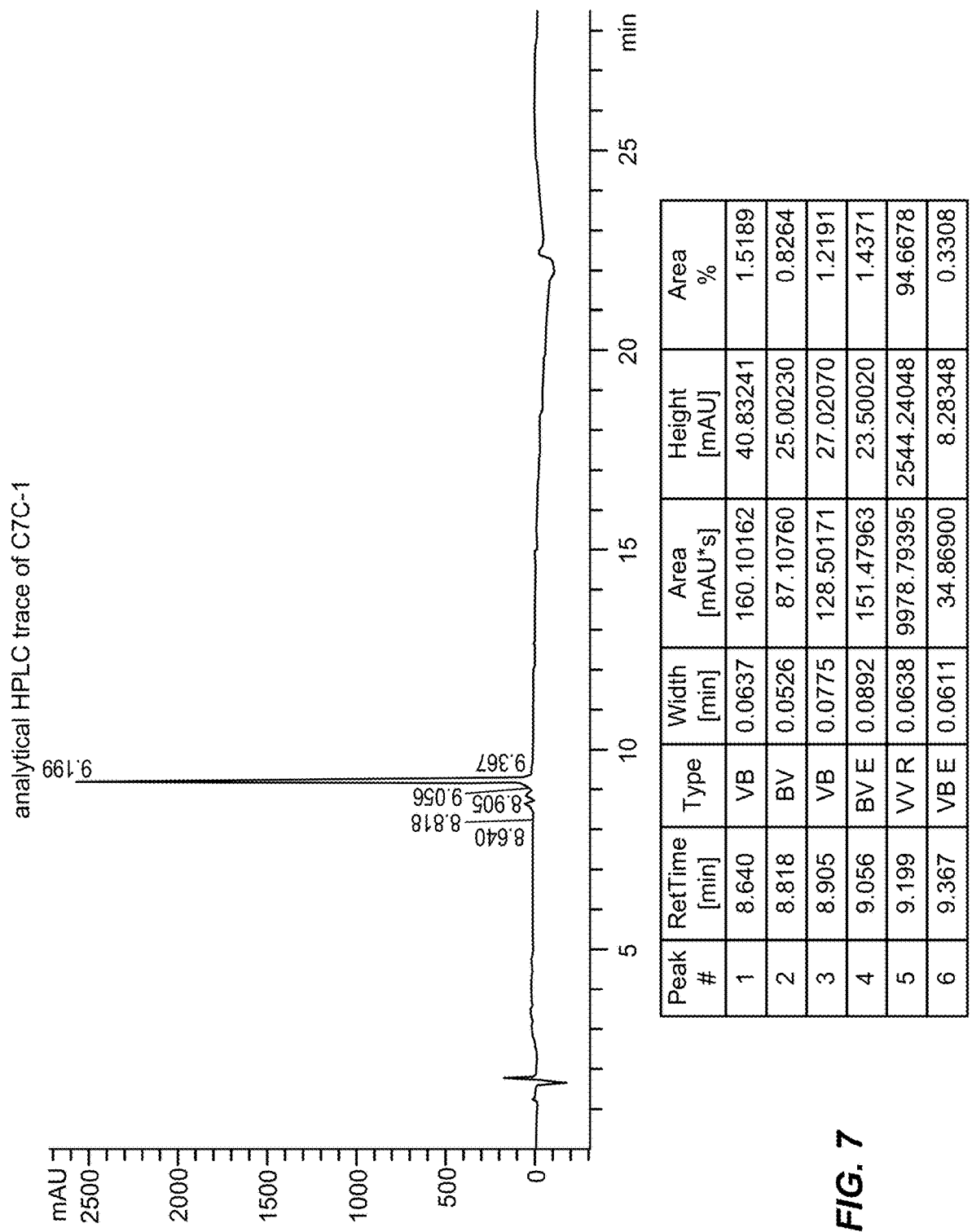
FIG. 7. Analysis of purity of C7C-1 by HPLC. Note that the purity is ~95%.

Peptide Synthesis—Peptides were synthesized by automated solid-phase peptide synthesis by Sigma-Aldrich, with the exception of C7C-1, which was synthesized in-house essentially as described (28) and analyzed by electrospray-ionization mass spectrometry (ESI-MS; FIG. 6) and HPLC (FIG. 7). Cosmetic-grade, gram-scale quantities of P12-3A were synthesized by GenScript Biotechnology Corp. (Piscataway Township, NJ, USA).

Degradation Assays—IDE activity was quantified by monitoring the degradation of (7-methoxycoumarin-4-yl) acetic acid-GGFLRKVGQK(2,4-dinitrophenyl) (FRET1, 5 µM) (49,55), fluoresceinated and biotinylated amyloid β-protein (FAβB; 500 nM) or recombinant human insulin (50 nM) in PBS supplemented with 0.05% BSA. FRET1 degradation was measured by changes in fluorescence ($\lambda_{ex}$=340 nm, $\lambda_{em}$=420 nm); FAβB degradation was monitored by fluorescence polarization ($\lambda_{ex}$=488 nm, $\lambda_{em}$=525 nm), as described (56); and insulin degradation was quantified by ELISA. In vitro activity assays incorporated recombinant human IDE (1 nM) purified from bacteria (35). For quantitation of insulin degradation in primary murine skin fibroblasts, cells ($1 \times 10^5$/well) were plated in 96-well plates and maintained in DMEM supplemented with 10% fetal bovine serum (FBS), 2 mM glutamine, penicillin and streptomycin. After addition of insulin (10 nM or 100 nM), samples of conditioned medium were removed daily and quickly frozen, then insulin levels were quantified in parallel by ELISA according to manufacturer's recommendations (Crystal Chem, Downers Grove, Ill., USA). Assessment of the activity of P12-3A against a variety of matrix-metalloproteases was conducted using the Matrix Metalloproteinase (MMP) Inhibitor Profiling Kit, Fluorometric RED (Enzo Life Sciences, Inc., Farmingdale, N.Y., USA) according to manufacturer's recommendations using the broad-spectrum MMP inhibitor, NNGH, as a positive control. Activity assays on additional proteases were conducted using the FAβB degradation assay, using a custom protease inhibitor cocktail (PIC) comprised of cOmplete™, Mini, EDTA-free Protease Inhibitor Cocktail supplemented with 1,10-phenanthroline (2 mM) and pepstatin A (5 µM).

Cell Proliferation—Primary murine skin fibroblasts cells ($1 \times 10^5$/well) were plated in 96-well plates, using separate plates for each timepoint and endpoint. Cell proliferation was quantified using the CellTiter 96® AQueous Non-Radioactive Cell Proliferation Assay (Promega Corp., Madison, Wis., USA) according to manufacturer's recommendations.

RNA Quantification—RNA was extracted from freshly lysed cells, reverse transcribed and amplified using the Ambion® Fast SYBR® Green Cells-to-CT™ Kit according to manufacturer's recommendations (Thermo Fisher Scientific, Waltham, Mass., USA). The quantitative real-time PCR reaction was conducted using a 7500 real time PCR system and analyzed using System SDS software v2.0.5 (Applied Biosystems). Murine COL1A1 mRNA was detected using the following primers (forward: 5'-ACCTAAGGG-TACCGCTGGA [SEQ ID NO:23] and reverse: 5' TCCAGCTTCTCCATCTTTGC [SEQ ID NO:24]). Fold change differences between samples were determined using the comparative $C_t$ ($\Delta\Delta C_t$) method, normalized to internal standards detected with the SYBR® Green Cells-to-$C_T$™ Control Kit according to manufacturer's recommendations (Thermo Fisher Scientific, Waltham, Mass., USA) calculated by $2^{-\Delta\Delta Ct}$.

Western Blotting—Protein was collected using the M-Per Mammalian Extraction Reagent and the concentration was quantified using the Pierce™ BCA Protein Assay Kit according to manufacturer's recommendations (Thermo Fisher Scientific, Waltham, Mass., USA). Protein (30 µg/well) was separated SDS-PAGE under reducing conditions using Novex™ 10% polyacrylamide tris-glycine mini gels and transferred to nitrocellulose membranes as described (57). Briefly, membranes were blocked in 5% non-fat milk in tris-buffered saline supplemented with 0.2% Tween-20 (TBST), cut into segments and incubated for 1 h at room temperature with anti-alpha-1 type I collagen (1:5000) and anti-GAPDH (1:10,000) antibodies, washed extensively in TBST, then probed with anti-rabbit (1:20,000) or anti-goat (1:50,000) secondary antibodies, respectively, and detected by enhanced chemoluminescence using Super-Signal West Pico Substrate. Protein expression, normalized to GAPDH levels, was quantified using the band analysis tools of ImageLab software, version 4.1 (Bio-Rad Laboratories, Inc., Hercules, Calif., USA).

In Vitro Scratch Wound Assay—Cell migration in HaCaT cells after induction of scratch wounds was quantified essentially as described (58). Briefly, HaCaT cells maintained in optimized DMEM (AddexBio Technologies, San Diego, Calif., USA) supplemented with 10% FBS, penicillin and streptomycin, were grown to confluency in 24-well tissue culture plates, and scratch wounds were induced with a 200-4, pipette tip. After growth for 48 h in the absence or presence of insulin (10 nM or 100 nM) and/or P12-3A (100 µM), cell migration distance was quantified by two independent, blinded observers using a Nikon TMS inverted light microscope (Nikon Corp., Melville, N.Y., USA) fitted with a ruler reticle.

Statistical Analyses—Tests for statistical significance were performed by using the two-tailed Student's t test with various levels of significance (P=0.05, 0.01). For comparisons with unequal numbers of replications per group, Hartley's Fmax was calculated to check for homogeneity of variance. All calculations and curve fitting were performed in Prism for Mac OS X, version 5.0b (GraphPad Software, Inc., La Jolla, Calif., USA).

REFERENCES

1. Hrynyk, M., and Neufeld, R. J. (2014) Insulin and wound healing. *Burns* 40, 1433-1446
2. Aaronson, S. A., Rubin, J. S., Finch, P. W., Wong, J., Marchese, C., Falco, J., Taylor, W. G., and Kraus, M. H. (1990) Growth factor-regulated pathways in epithelial cell proliferation. *Am. Rev. Respir. Dis.* 142, S7-10
3. Monaco, S., Illario, M., Rusciano, M. R., Gragnaniello, G., Di Spigna, G., Leggiero, E., Pastore, L., Fenzi, G., Rossi, G., and Vitale, M. (2009) Insulin stimulates fibroblast proliferation through calcium-calmodulin-dependent kinase II. *Cell Cycle* 8, 2024-2030
4. Wertheimer, E., Trebicz, M., Eldar, T., Gartsbein, M., Nofeh-Moses, S., and Tennenbaum, T. (2000) Differential roles of insulin receptor and insulin-like growth factor-1 receptor in differentiation of murine skin keratinocytes. *J. Invest. Dermatol.* 115, 24-29
5. Benoliel, A. M., Kahn-Perles, B., Imbert, J., and Verrando, P. (1997) Insulin stimulates haptotactic migration of human epidermal keratinocytes through activation of NF-kappa B transcription factor. *J. Cell Sci.* 110 (Pt 17), 2089-2097
6. Liu, Y., Petreaca, M., Yao, M., and Martins-Green, M. (2009) Cell and molecular mechanisms of keratinocyte function stimulated by insulin during wound healing. *BMC Cell Biol.* 10, 1
7. Villee, D. B., and Powers, M. L. (1977) Effect of glucose and insulin on collagen secretion by human skin fibroblasts in vitro. *Nature* 268, 156-158
8. Kjellstrom, T., and Malmquist, J. (1984) Insulin effects on collagen and protein production in cultured human skin fibroblasts from diabetic and non-diabetic subjects. *Horm. Metab. Res.* 16, 168-171
9. Goldstein, R. H., Poliks, C. F., Pilch, P. F., Smith, B. D., and Fine, A. (1989) Stimulation of collagen formation by insulin and insulin-like growth factor I in cultures of human lung fibroblasts. *Endocrinology* 124, 964-970
10. Krupsky, M., Fine, A., Kuang, P. P., Berk, J. L., and Goldstein, R. H. (1996) Regulation of type I collagen production by insulin and transforming growth factor-beta in human lung fibroblasts. *Connect. Tissue Res.* 34, 53-62
11. Trevisan, R., Yip, J., Sarika, L., Li, L. K., and Viberti, G. (1997) Enhanced collagen synthesis in cultured skin fibroblasts from insulin-dependent diabetic patients with nephropathy. *J. Am. Soc. Nephrol.* 8, 1133-1139
12. Gore-Hyer, E., Pannu, J., Smith, E. A., Grotendorst, G., and Trojanowska, M. (2003) Selective stimulation of collagen synthesis in the presence of costimulatory insulin signaling by connective tissue growth factor in scleroderma fibroblasts. *Arthritis Rheum.* 48, 798-806
13. Musselmann, K., Kane, B., Alexandrou, B., and Hassell, J. R. (2006) Stimulation of collagen synthesis by insulin and proteoglycan accumulation by ascorbate in bovine keratocytes in vitro. *Invest. Ophthalmol. Vis. Sci.* 47, 5260-5266
14. Wertheimer, E., Spravchikov, N., Trebicz, M., Gartsbein, M., Accili, D., Avinoah, I., Nofeh-Moses, S., Sizyakov, G., and Tennenbaum, T. (2001) The regulation of skin proliferation and differentiation in the IR null mouse: implications for skin complications of diabetes. *Endocrinology* 142, 1234-1241
15. Baltzis, D., Eleftheriadou, I., and Veves, A. (2014) Pathogenesis and treatment of impaired wound healing in diabetes mellitus: new insights. *Adv. Ther.* 31, 817-836
16. Hanam, S. R., Singleton, C. E., and Rudek, W. (1983) The effect of topical insulin on infected cutaneous ulcerations in diabetic and nondiabetic mice. *J. Foot Surg.* 22, 298-301
17. Belfield, W. O., Golinsky, S., and Compton, M. D. (1970) The use of insulin in open-wound healing. *Vet. Med. Small Anim. Clin.* 65, 455-460
18. Weringer, E. J., Kelso, J. M., Tamai, I. Y., and Arquilla, E. R. (1982) Effects of insulin on wound healing in diabetic mice. *Acta Endocrinol.* (Copenh.) 99, 101-108
19. Madibally, S. V., Solomon, V., Mitchell, R. N., Van De Water, L., Yarmush, M. L., and Toner, M. (2003) Influence of insulin therapy on burn wound healing in rats. *J. Surg. Res.* 109, 92-100
20. Apikoglu-Rabus, S., Izzettin, F. V., Turan, P., and Ercan, F. (2010) Effect of topical insulin on cutaneous wound healing in rats with or without acute diabetes. *Clin. Exp. Dermatol.* 35, 180-185
21. Wilson, J. M., Baines, R., Babu, E. D., and Kelley, C. J. (2008) A role for topical insulin in the management problematic surgical wounds. *Ann. R. Coll. Surg. Engl.* 90, 160
22. Lima, M. H., Caricilli, A. M., de Abreu, L. L., Araujo, E. P., Pelegrinelli, F. F., Thirone, A. C., Tsukumo, D. M., Pessoa, A. F., dos Santos, M. F., de Moraes, M. A., Carvalheira, J. B., Velloso, L. A., and Saad, M. J. (2012) Topical insulin accelerates wound healing in diabetes by enhancing the AKT and ERK pathways: a double-blind placebo-controlled clinical trial. *Plos. One* 7, e36974
23. Greenway, S. E., Filler, L. E., and Greenway, F. L. (1999) Topical insulin in wound healing: a randomised, double-blind, placebo-controlled trial. *J. Wound Care* 8, 526-528
24. Rezvani, O., Shabbak, E., Aslani, A., Bidar, R., Jafari, M., and Safarnezhad, S. (2009) A randomized, double-blind, placebo-controlled trial to determine the effects of topical insulin on wound healing. *Ostomy. Wound Manage.* 55, 22-28
25. Coid, D. R. (1977) Hypoglycaemia during treatment of decubitus ulcer with topical insulin. *Br. Med. J.* 2, 1063-1064
26. Tang, W. J. (2016) Targeting Insulin-Degrading Enzyme to Treat Type 2 Diabetes Mellitus. *Trends Endocrinol. Metab.* 27, 24-34
27. Leal, M. C., and Morelli, L. (2013) Insulysin. in *Handbook of Proteolytic Enzymes* (Rawlings, N. D., and Salvesen, G. eds.), 3rd Ed., Academic Press. pp 1415-1420
28. Leissring, M. A., Malito, E., Hedouin, S., Reinstatler, L., Sahara, T., Abdul-Hay, S. O., Choudhry, S., Maharvi, G. M., Fauq, A. H., Huzarska, M., May, P. S., Choi, S., Logan, T. P., Turk, B. E., Cantley, L. C., Manolopoulou, M., Tang, W. J., Stein, R. L., Cuny, G. D., and Selkoe, D. J. (2010) Designed inhibitors of insulin-degrading enzyme regulate the catabolism and activity of insulin. *Plos. One* 5, e10504
29. Maianti, J. P., McFedries, A., Foda, Z. H., Kleiner, R. E., Du, X. Q., Leissring, M. A., Tang, W. J., Charron, M. J., Seeliger, M. A., Saghatelian, A., and Liu, D. R. (2014) Anti-diabetic activity of insulin-degrading enzyme inhibitors mediated by multiple hormones. *Nature* 511, 94-98
30. Mirsky, I. A., and Perisutti, G. (1955) Effect of insulinase-inhibitor on hypoglycemic action of insulin. *Science* 122, 559-560
31. Mirsky, I. A., Perisutti, G., and Diengott, D. (1955) Effect of insulinase-inhibitor on destruction of insulin by intact mouse. *Proc. Soc. Exp. Biol. Med.* 88, 76-78
32. Abdul-Hay, S. O., Kang, D., McBride, M., Li, L., Zhao, J., and Leissring, M. A. (2011) Deletion of insulindegrading enzyme elicits antipodal, age-dependent effects on glucose and insulin tolerance. *Plos. One* 6, e20818
33. Farris, W., Mansourian, S., Chang, Y., Lindsley, L., Eckman, E. A., Frosch, M. P., Eckman, C. B., Tanzi, R. E., Selkoe, D. J., and Guenette, S. (2003) Insulin-degrading enzyme regulates the levels of insulin, amyloid beta-protein, and the beta-amyloid precursor protein intracellular domain in vivo. *Proc. Natl. Acad. Sci. U.S.A.* 100, 4162-4167
34. Miller, B. C., Eckman, E. A., Sambamurti, K., Dobbs, N., Chow, K. M., Eckman, C. B., Hersh, L. B., and Thiele, D. L. (2003) Amyloid-beta peptide levels in brain are inversely correlated with insulysin activity levels in vivo. *Proc. Natl. Acad. Sci. U.S.A.* 100, 6221-6226
35. Farris, W., Leissring, M. A., Hemming, M. L., Chang, A. Y., and Selkoe, D. J. (2005) Alternative splicing of human insulin-degrading enzyme yields a novel isoform with a decreased ability to degrade insulin and amyloid beta-protein. *Biochemistry* 44, 6513-6525
36. Kuo, W. L., Montag, A. G., and Rosner, M. R. (1993) Insulin-degrading enzyme is differentially expressed and developmentally regulated in various rat tissues. *Endocrinology* 132, 604-611
37. Shearer, J. D., Coulter, C. F., Engeland, W. C., Roth, R. A., and Caldwell, M. D. (1997) Insulin is degraded extracellularly in wounds by insulin-degrading enzyme (EC 3.4.24.56). *Am. J. Physiol.* 273, E657-664
38. Duckworth, W. C., Fawcett, J., Reddy, S., and Page, J. C. (2004) Insulin-degrading activity in wound fluid. *J. Clin. Endocrinol. Metab.* 89, 847-851
39. Durham, T. B., Toth, J. L., Klimkowski, V. J., Cao, J. X., Siesky, A. M., Alexander-Chacko, J., Wu, G. Y., Dixon, J. T., McGee, J. E., Wang, Y., Guo, S. Y., Cavitt, R. N., Schindler, J., Thibodeaux, S. J., Calvert, N. A., Coghlan, M. J., Sindelar, D. K., Christe, M., Kiselyov, V. V., Michael, M. D., and Sloop, K. W. (2015) Dual exosite-binding inhibitors of insulin-degrading enzyme challenge its role as the primary mediator of insulin clearance in vivo. *J. Biol. Chem.* 290, 20044-20059
40. Charton, J., Gauriot, M., Totobenazara, J., Hennuyer, N., Dumont, J., Bosc, D., Marechal, X., Elbakali, J., Herledan, A., Wen, X., Ronco, C., Gras-Masse, H., Heninot, A., Pottiez, V., Landry, V., Staels, B., Liang, W. G., Leroux, F., Tang, W. J., Deprez, B., and Deprez-Poulain, R. (2015) Structure-activity relationships of imidazole-derived 2[N-carbamoylmethyl-alkylamino]acetic acids, dual binders of human insulin-degrading enzyme. *Eur. J. Med. Chem.* 90, 547-567
41. Abdul-Hay, S. O., Bannister, T. D., Wang, H., Cameron, M. D., Caulfield, T. R., Masson, A., Bertrand, J., Howard, E. A., McGuire, M. P., Crisafulli, U., Rosenberry, T. R., Topper, C. L., Thompson, C. R., Schurer, S. C., Madoux, F., Hodder, P., and Leissring, M. A. (2015) Selective targeting of extracellular insulin-degrading enzyme by quasi-irreversible thiol-modifying inhibitors. *ACS Chem. Biol.* 10, 2716-2724
42. Charton, J., Gauriot, M., Guo, Q., Hennuyer, N., Marechal, X., Dumont, J., Hamdane, M., Pottiez, V., Landry, V., Sperandio, O., Flipo, M., Buee, L., Staels, B., Leroux, F., Tang, W. J., Deprez, B., and Deprez-Poulain, R. (2014) Imidazole-derived 2[N-carbamoylmethyl-alkylamino] acetic acids, substrate-dependent modulators of insulin-degrading enzyme in amyloid-beta hydrolysis. *Eur. J. Med. Chem.* 79, 184-193
43. Abdul-Hay, S. O., Lane, A. L., Caulfield, T. R., Claussin, C., Bertrand, J., Masson, A., Choudhry, S., Fauq, A. H., Maharvi, G. M., and Leissring, M. A. (2013) Optimization of peptide hydroxamate inhibitors of insulin-degrading enzyme reveals marked substrate-selectivity. *J. Med. Chem.* 56, 2246-2255
44. Smith, G. P. (1985) Filamentous fusion phage: novel expression vectors that display cloned antigens on the virion surface. *Science* 228, 1315-1317
45. Cabrol, C., Huzarska, M. A., Dinolfo, C., Rodriguez, M. C., Reinstatler, L., Ni, J., Yeh, L. A., Cuny, G. D., Stein, R. L., Selkoe, D. J., and Leissring, M. A. (2009) Small-molecule activators of insulin-degrading enzyme discovered through high-throughput compound screening. *Plos. One* 4, e5274
46. Cheng, Y., and Prusoff, W. H. (1973) Relationship between the inhibition constant (K1) and the concentration of inhibitor which causes 50 percent inhibition (IS0) of an enzymatic reaction. *Biochem. Pharmacol.* 22, 3099-3108
47. Gordon, M. K., and Hahn, R. A. (2010) Collagens. *Cell Tissue Res.* 339, 247-257
48. Bannister, T. D., Wang, H., Abdul-Hay, S. O., Masson, A., Madoux, F., Ferguson, J., Mercer, B. A., Schurer, S., Zuhl, A., Cravat, B. F., Leissring, M. A., and Hodder, P. (2010) ML345, A Small-Molecule Inhibitor of the Insulin-Degrading Enzyme (IDE). in Probe Reports from the NIH Molecular Libraries Program, Bethesda (Md.). pp
49. Neant-Fery, M., Garcia-Ordonez, R. D., Logan, T. P., Selkoe, D. J., Li, L., Reinstatler, L., and Leissring, M. A. (2008) Molecular basis for the thiol sensitivity of insulin-degrading enzyme. *Proc. Natl. Acad. Sci. U.S.A.* 105, 9582-9587
50. Shen, Y., Joachimiak, A., Rosner, M. R., and Tang, W. J. (2006) Structures of human insulin-degrading enzyme reveal a new substrate recognition mechanism. *Nature* 443, 870-874
51. Leissring, M. A., and Selkoe, D. J. (2006) Structural biology: enzyme target to latch on to. *Nature* 443, 761-762
52. Singh, A., and Yadav, S. (2016) Microneedling: Advances and widening horizons. *Indian Dermatol. Online J.* 7, 244-254
53. Aust, M. C., Fernandes, D., Kolokythas, P., Kaplan, H. M., and Vogt, P. M. (2008) Percutaneous collagen induction therapy: an alternative treatment for scars, wrinkles, and skin laxity. *Plast. Reconstr. Surg.* 121, 1421-1429
54. Fernandes, D. (2005) Minimally invasive percutaneous collagen induction. *Oral Maxillofac. Surg. Clin. North Am.* 17, 51-63, vi
55. Im, H., Manolopoulou, M., Malito, E., Shen, Y., Zhao, J., Neant-Fery, M., Sun, C. Y., Meredith, S. C., Sisodia, S. S., Leissring, M. A., and Tang, W. J. (2007) Structure of substrate-free human insulin-degrading enzyme (IDE) and biophysical analysis of ATP-induced conformational switch of IDE. *J. Biol. Chem.* 282, 25453-25463
56. Leissring, M. A., Lu, A., Condron, M. M., Teplow, D. B., Stein, R. L., Farris, W., and Selkoe, D. J. (2003) Kinetics of amyloid beta-protein degradation determined by novel fluorescence- and fluorescence polarization-based assays. *J. Biol. Chem.* 278, 37314-37320
57. Delledonne, A., Kouri, N., Reinstatler, L., Sahara, T., Li, L., Zhao, J., Dickson, D. W., Ertekin-Taner, N., and Leissring, M. A. (2009) Development of monoclonal antibodies and quantitative ELISAs targeting insulin-degrading enzyme. *Mol. Neurodegen.* 4, 39
58. Liang, C. C., Park, A. Y., and Guan, J. L. (2007) In vitro scratch assay: a convenient and inexpensive method for analysis of cell migration in vitro. *Nat. Protoc.* 2, 329-333

What is claimed is:

1. An:
   isolated peptide of 30 amino acid residues or less, wherein the peptide comprises a peptide amino acid sequence, said peptide amino acid sequence comprising or consisting of an amino acid sequence having at least 80% sequence identity to an amino acid sequence selected from the group consisting of:
   QSLPWCYPHCVT (SEQ ID NO:1),
   ACSWWSIHLCG (SEQ ID NO:3), and
   WSPISGKFFQRF (SEQ ID NO:4); or
   isolated peptoid thereof.

2. The peptide or peptoid of claim 1, wherein the peptide or peptoid inhibits the proteolytic activity of insulin-degrading enzyme (IDE).

3. The peptide or peptoid of claim 1, wherein the peptide comprises not more than 15 amino acid residues.

4. The peptide or peptoid of claim 1, wherein the peptide comprises all L-isomer amino acid residues.

5. The peptide or peptoid of claim 1, wherein the peptide comprises one or more D-isomer amino acid residues.

6. The peptide or peptoid of claim 1, wherein the peptide or peptoid is cyclized.

7. The peptide or peptoid of claim 1, wherein the peptide or peptoid comprises a modification other than cyclization that increases stability.

8. The peptide or peptoid of claim 7, wherein the peptide comprises one or more N-methyl amino acid residues.

9. The peptide or peptoid of claim 1, wherein the peptide comprises one or more beta-amino acid residues.

10. The peptide or peptoid of claim 1, wherein the peptide bears no terminal protecting groups.

11. The peptide or peptoid of claim 1, wherein the peptide comprises one or more terminal protecting groups.

12. The peptide or peptoid of claim 11, wherein said one or more protecting groups are independently selected from the group consisting of acetyl, amide, 3 to 20 carbon alkyl groups, fluorenylmethyloxycarbonyl (Fmoc), 9-fluoreneacetyl group, 1-fluorenecarboxylic group, 9-fluorenecarboxylic group, 9-fluorenone-1-carboxylic group, benzyloxycarbonyl, xanthyl (Xan), trityl (Trt), 4-methyltrityl (Mtt), 4-methoxytrityl (Mmt), 4-methoxy-2,3,6-trimethyl-benzenesulphonyl (Mtr), mesitylene-2-sulphonyl (Mts), 4,4-dimethoxybenzhydryl (Mbh), tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), benzyloxymethyl (Bom), t-butyloxycarbonyl (Tboc), cyclohexyloxy (cHxO), t-butoxymethyl (Bum), t-butoxy (tBuO), t-butyl (tBu), and trifluoroacetyl (TFA).

13. The peptide or peptoid of claim 11, wherein the peptide comprises a protecting group at a carboxyl terminus and an amino terminus.

14. The peptide or peptoid of claim 1, wherein the peptide amino acid sequence comprises or consists of QSLPWCYPHCVT (SEQ ID NO:1), and the peptide additionally comprises an amide group at the C-terminus of the peptide.

15. The peptide or peptoid according to claim 1, wherein said peptide or peptoid is functionalized with a polymer to increase its stability in a biological milieu.

16. The peptide or peptoid of claim 1, wherein the peptide or peptoid is a peptide.

17. The peptide of claim 16, wherein the peptide comprises the peptide amino acid sequence QSLPWCYPHCVT (SEQ ID NO:1).

18. The peptide of claim 17, wherein the peptide consists of the peptide amino acid sequence QSLPWCYPHCVT (SEQ ID NO:1).

19. A cosmetic or pharmaceutical formulation comprising the peptide or peptoid of claim 1 and a carrier.

20. The cosmetic or pharmaceutical formulation of claim 19, wherein the cosmetic or pharmaceutical formulation is sterile.

21. The cosmetic or pharmaceutical formulation of claim 19, wherein the peptide comprises or consists of the peptide amino acid sequence QSLPWCYPHCVT (SEQ ID NO:1).

22. A method of improving the appearance and/or texture of skin and/or promoting wound healing in a living subject, wherein the method comprises topically administering a peptide or peptoid to the skin of the subject, wherein:
the peptide is 30 amino acid residues or less and comprises a peptide amino acid sequence, said peptide amino acid sequence comprising or consisting of an amino acid sequence having at least 80% sequence identity to an amino acid sequence selected from the group consisting of:

QSLPWCYPHCVT, (SEQ ID NO: 1)

VHWDFRQWWQPS, (SEQ ID NO: 2)

ACSWWSIHLCG, (SEQ ID NO: 3)
and

WSPISGKFFQRF; (SEQ ID NO: 4)

and
the peptoid is a peptoid of said peptide.

23. The method of improving the appearance and/or texture of skin and/or promoting wound healing in a living subject of claim 22, wherein the peptide comprises or consists of the peptide amino acid sequence QSLPWCYPHCVT (SEQ ID NO:1).

24. A method of treating diabetes, wherein the method comprises administering an effective amount of a peptide or peptoid to a subject having diabetes, wherein:
the peptide is 30 amino acid residues or less and comprises a peptide amino acid sequence, said peptide amino acid sequence comprising or consisting of an amino acid sequence having at least 80% sequence identity to an amino acid sequence selected from the group consisting of:

QSLPWCYPHCVT, (SEQ ID NO: 1)

VHWDFRQWWQPS, (SEQ ID NO: 2)

ACSWWSIHLCG, (SEQ ID NO: 3)
and

WSPISGKFFQRF. (SEQ ID NO: 4)

and
the peptoid is a peptoid of said peptide.

25. The method of treating diabetes of claim 24, wherein the peptide comprises or consists of the peptide amino acid sequence QSLPWCYPHCVT (SEQ ID NO:1).

* * * * *

SEQUENCE LISTING

<160> NUMBER OF SEQ ID NOS: 66

<210> SEQ ID NO 1
<211> LENGTH: 12
<212> TYPE: PRT
<213> ORGANISM: Artificial
<220> FEATURE:
<223> OTHER INFORMATION: synthesized peptide sequences selected from a
      phage display library

<400> SEQUENCE: 1

Gln Ser Leu Pro Trp Cys Tyr Pro His Cys Val Thr
1               5                   10

<210> SEQ ID NO 2
<211> LENGTH: 12
<212> TYPE: PRT
<213> ORGANISM: Artificial
<220> FEATURE:
<223> OTHER INFORMATION: synthesized peptide sequences selected from a
      phage display library

<400> SEQUENCE: 2

Val His Trp Asp Phe Arg Gln Trp Trp Gln Pro Ser
1               5                   10

<210> SEQ ID NO 3
<211> LENGTH: 11
<212> TYPE: PRT
<213> ORGANISM: Artificial
<220> FEATURE:
<223> OTHER INFORMATION: synthesized peptide sequences selected from a
      phage display library

<400> SEQUENCE: 3

Ala Cys Ser Trp Trp Ser Ile His Leu Cys Gly
1               5                   10

<210> SEQ ID NO 4
<211> LENGTH: 12
<212> TYPE: PRT
<213> ORGANISM: Artificial
<220> FEATURE:
<223> OTHER INFORMATION: synthesized peptide sequences selected from a
      phage display library

<400> SEQUENCE: 4

Trp Ser Pro Ile Ser Gly Lys Phe Phe Gln Arg Phe
1               5                   10

<210> SEQ ID NO 5
<211> LENGTH: 13
<212> TYPE: PRT
<213> ORGANISM: Artificial
<220> FEATURE:
<223> OTHER INFORMATION: synthesized peptide sequences selected from a
      phage display library

<400> SEQUENCE: 5

Ala Cys Asn Asn Asn Asn Asn Asn Cys Gly Gly Gly
1               5                   10

<210> SEQ ID NO 6
<211> LENGTH: 13
<212> TYPE: PRT
<213> ORGANISM: Artificial
<220> FEATURE:
<223> OTHER INFORMATION: synthesized peptide sequences selected from a phage display library

<400> SEQUENCE: 6

Ala Cys Ser Trp Trp Ser Ile His Leu Cys Gly Gly Gly
1               5                   10

<210> SEQ ID NO 7
<211> LENGTH: 13
<212> TYPE: PRT
<213> ORGANISM: Artificial
<220> FEATURE:
<223> OTHER INFORMATION: synthesized peptide sequences selected from a
      phage display library

<400> SEQUENCE: 7

Ala Cys Asn Ala Gly His Leu Ser Gln Cys Gly Gly Gly
1               5                   10

<210> SEQ ID NO 8
<211> LENGTH: 11
<212> TYPE: PRT
<213> ORGANISM: Artificial
<220> FEATURE:
<223> OTHER INFORMATION: synthesized peptide sequences selected from a
      phage display library

<400> SEQUENCE: 8

Ala Cys Asn Ala Gly His Leu Ser Gln Cys Gly
1               5                   10

<210> SEQ ID NO 9
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 9

Val His Trp Asp Phe Arg Gln Trp
1               5

<210> SEQ ID NO 10
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 10

Phe Arg Gln Trp Trp Gln Pro Ser
1               5

<210> SEQ ID NO 11
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 11

Trp Asp Phe Arg Gln Trp Trp Gln
1               5

<210> SEQ ID NO 12

```
<211> LENGTH: 12
<212> TYPE: PRT
<213> ORGANISM: Artificial
<220> FEATURE:
<223> OTHER INFORMATION: synthesized peptide sequences selected from a
      phage display library

<400> SEQUENCE: 12

Leu Asn Phe Pro Met Pro Ser Arg Pro His Ser Ser
1               5                   10

<210> SEQ ID NO 13
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 13

Leu Asn Phe Pro Met Pro Ser Arg
1               5

<210> SEQ ID NO 14
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 14

Met Pro Ser Arg Pro His Ser Ser
1               5

<210> SEQ ID NO 15
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 15

Phe Pro Met Pro Ser Arg Pro His
1               5

<210> SEQ ID NO 16
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 16

Gln Ser Leu Pro Trp Cys Tyr Pro
1               5

<210> SEQ ID NO 17
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 17
```

Trp Cys Tyr Pro His Cys Val Thr
1               5

<210> SEQ ID NO 18
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 18

Leu Pro Trp Cys Thr Pro His Cys
1               5

<210> SEQ ID NO 19
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 19

Trp Ser Pro Ile Ser Gly Lys Phe
1               5

<210> SEQ ID NO 20
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 20

Ser Gly Lys Phe Phe Gln Arg Phe
1               5

<210> SEQ ID NO 21
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 21

Pro Ile Ser Gly Lys Phe Phe Gln
1               5

<210> SEQ ID NO 22
<211> LENGTH: 10
<212> TYPE: PRT
<213> ORGANISM: Artificial
<220> FEATURE:
<223> OTHER INFORMATION: synthesized peptide sequences selected from a
      phage display library

<400> SEQUENCE: 22

Gly Gly Phe Leu Arg Lys Val Gly Gln Lys
1               5                   10

<210> SEQ ID NO 23
<211> LENGTH: 19
<212> TYPE: DNA
<213> ORGANISM: Artificial
<220> FEATURE:

<223> OTHER INFORMATION: primer

<400> SEQUENCE: 23
acctaagggt accgctgga                                                  19

<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24
tccagcttct ccatctttgc                                                 20

<210> SEQ ID NO 25
<211> LENGTH: 9
<212> TYPE: PRT
<213> ORGANISM: Artificial
<220> FEATURE:
<223> OTHER INFORMATION: synthesized peptide sequences selected from a
      phage display library

<400> SEQUENCE: 25

Cys Asn Trp Met Asn Ile His Met Cys
1               5

<210> SEQ ID NO 26
<211> LENGTH: 9
<212> TYPE: PRT
<213> ORGANISM: Artificial
<220> FEATURE:
<223> OTHER INFORMATION: synthesized peptide sequences selected from a
      phage display library

<400> SEQUENCE: 26

Cys Ser Lys Asn Phe Pro Arg Asn Cys
1               5

<210> SEQ ID NO 27
<211> LENGTH: 9
<212> TYPE: PRT
<213> ORGANISM: Artificial
<220> FEATURE:
<223> OTHER INFORMATION: synthesized peptide sequences selected from a
      phage display library

<400> SEQUENCE: 27

Cys Asp Trp Met Arg Ile Trp Asn Cys
1               5

<210> SEQ ID NO 28
<211> LENGTH: 9
<212> TYPE: PRT
<213> ORGANISM: Artificial
<220> FEATURE:
<223> OTHER INFORMATION: synthesized peptide sequences selected from a
      phage display library

<400> SEQUENCE: 28

Cys Ile His Ser Pro Thr Ala Leu Cys
1               5

<210> SEQ ID NO 29
<211> LENGTH: 9
<212> TYPE: PRT
<213> ORGANISM: Artificial

```
<220> FEATURE:
<223> OTHER INFORMATION: synthesized peptide sequences selected from a
      phage display library

<400> SEQUENCE: 29

Cys Leu Pro Trp Pro Leu Ser Leu Cys
1               5

<210> SEQ ID NO 30
<211> LENGTH: 9
<212> TYPE: PRT
<213> ORGANISM: Artificial
<220> FEATURE:
<223> OTHER INFORMATION: synthesized peptide sequences selected from a
      phage display library

<400> SEQUENCE: 30

Cys Ser Trp Trp Met Leu His His Cys
1               5

<210> SEQ ID NO 31
<211> LENGTH: 9
<212> TYPE: PRT
<213> ORGANISM: Artificial
<220> FEATURE:
<223> OTHER INFORMATION: synthesized peptide sequences selected from a
      phage display library

<400> SEQUENCE: 31

Cys Ser Trp Trp Asn Ile His Leu Cys
1               5

<210> SEQ ID NO 32
<211> LENGTH: 9
<212> TYPE: PRT
<213> ORGANISM: Artificial
<220> FEATURE:
<223> OTHER INFORMATION: synthesized peptide sequences selected from a
      phage display library

<400> SEQUENCE: 32

Cys Leu Trp Trp Gln Leu His Leu Cys
1               5

<210> SEQ ID NO 33
<211> LENGTH: 9
<212> TYPE: PRT
<213> ORGANISM: Artificial
<220> FEATURE:
<223> OTHER INFORMATION: synthesized peptide sequences selected from a
      phage display library

<400> SEQUENCE: 33

Cys Ser Trp Met Ser Ile His Leu Cys
1               5

<210> SEQ ID NO 34
<211> LENGTH: 9
<212> TYPE: PRT
<213> ORGANISM: Artificial
<220> FEATURE:
<223> OTHER INFORMATION: synthesized peptide sequences selected from a
      phage display library

<400> SEQUENCE: 34

Cys Gly Phe Thr Thr Thr Phe Val Cys
1               5
```

<210> SEQ ID NO 35
<211> LENGTH: 9
<212> TYPE: PRT
<213> ORGANISM: Artificial
<220> FEATURE:
<223> OTHER INFORMATION: synthesized peptide sequences selected from a
      phage display library

<400> SEQUENCE: 35

Cys Asn Ala Gly His Leu Ser Gln Cys
1               5

<210> SEQ ID NO 36
<211> LENGTH: 9
<212> TYPE: PRT
<213> ORGANISM: Artificial
<220> FEATURE:
<223> OTHER INFORMATION: synthesized peptide sequences selected from a
      phage display library

<400> SEQUENCE: 36

Cys Ser Trp Trp Ser Ile His Val Cys
1               5

<210> SEQ ID NO 37
<211> LENGTH: 9
<212> TYPE: PRT
<213> ORGANISM: Artificial
<220> FEATURE:
<223> OTHER INFORMATION: synthesized peptide sequences selected from a
      phage display library

<400> SEQUENCE: 37

Cys Leu Leu Leu Leu Asn Asn Thr Cys
1               5

<210> SEQ ID NO 38
<211> LENGTH: 9
<212> TYPE: PRT
<213> ORGANISM: Artificial
<220> FEATURE:
<223> OTHER INFORMATION: synthesized peptide sequences selected from a
      phage display library

<400> SEQUENCE: 38

Cys Asn Trp Trp Thr Ile His Asn Cys
1               5

<210> SEQ ID NO 39
<211> LENGTH: 9
<212> TYPE: PRT
<213> ORGANISM: Artificial
<220> FEATURE:
<223> OTHER INFORMATION: synthesized peptide sequences selected from a
      phage display library

<400> SEQUENCE: 39

Cys Asn Ser Ile Lys Lys Trp Ser Cys
1               5

<210> SEQ ID NO 40
<211> LENGTH: 9
<212> TYPE: PRT
<213> ORGANISM: Artificial
<220> FEATURE:
<223> OTHER INFORMATION: synthesized peptide sequences selected from a
      phage display library

```
<400> SEQUENCE: 40

Cys Ile Ser Ser Ser Ile Asn His Cys
1               5

<210> SEQ ID NO 41
<211> LENGTH: 9
<212> TYPE: PRT
<213> ORGANISM: Artificial
<220> FEATURE:
<223> OTHER INFORMATION: synthesized peptide sequences selected from a
      phage display library

<400> SEQUENCE: 41

Cys Ser Trp Trp Ser Ile His Leu Cys
1               5

<210> SEQ ID NO 42
<211> LENGTH: 12
<212> TYPE: PRT
<213> ORGANISM: Artificial
<220> FEATURE:
<223> OTHER INFORMATION: synthesized peptide sequences selected from a
      phage display library

<400> SEQUENCE: 42

Asn Gln Leu Leu Thr Gln Arg Thr Pro Phe Gln Asp
1               5                   10

<210> SEQ ID NO 43
<211> LENGTH: 12
<212> TYPE: PRT
<213> ORGANISM: Artificial
<220> FEATURE:
<223> OTHER INFORMATION: synthesized peptide sequences selected from a
      phage display library

<400> SEQUENCE: 43

Ser Ser Asn Val Ile Ser Pro Phe Glu Gln Leu Leu
1               5                   10

<210> SEQ ID NO 44
<211> LENGTH: 12
<212> TYPE: PRT
<213> ORGANISM: Artificial
<220> FEATURE:
<223> OTHER INFORMATION: synthesized peptide sequences selected from a
      phage display library

<400> SEQUENCE: 44

Asn Ser Pro Ser Gly Leu Ile Gly Trp Thr Ser Arg
1               5                   10

<210> SEQ ID NO 45
<211> LENGTH: 12
<212> TYPE: PRT
<213> ORGANISM: Artificial
<220> FEATURE:
<223> OTHER INFORMATION: synthesized peptide sequences selected from a
      phage display library

<400> SEQUENCE: 45

Trp Val Pro Trp Ser Tyr Glu Tyr Phe Val Ser Thr
1               5                   10

<210> SEQ ID NO 46
<211> LENGTH: 12
<212> TYPE: PRT
```

<213> ORGANISM: Artificial
<220> FEATURE:
<223> OTHER INFORMATION: synthesized peptide sequences selected from a
      phage display library

<400> SEQUENCE: 46

Gly Pro Tyr Val Leu Gly Glu His Leu Arg Ser Asn
1               5                   10

<210> SEQ ID NO 47
<211> LENGTH: 12
<212> TYPE: PRT
<213> ORGANISM: Artificial
<220> FEATURE:
<223> OTHER INFORMATION: synthesized peptide sequences selected from a
      phage display library

<400> SEQUENCE: 47

Ser Pro Leu Trp Ser Gly Trp Ala Leu Glu Ile Leu
1               5                   10

<210> SEQ ID NO 48
<211> LENGTH: 12
<212> TYPE: PRT
<213> ORGANISM: Artificial
<220> FEATURE:
<223> OTHER INFORMATION: synthesized peptide sequences selected from a
      phage display library

<400> SEQUENCE: 48

Ser Phe Thr Trp Leu His Gly Ser Leu Thr Glu Arg
1               5                   10

<210> SEQ ID NO 49
<211> LENGTH: 12
<212> TYPE: PRT
<213> ORGANISM: Artificial
<220> FEATURE:
<223> OTHER INFORMATION: synthesized peptide sequences selected from a
      phage display library

<400> SEQUENCE: 49

Ser Asn Thr Gln Asn Val Tyr Trp Glu Arg Trp Ile
1               5                   10

<210> SEQ ID NO 50
<211> LENGTH: 12
<212> TYPE: PRT
<213> ORGANISM: Artificial
<220> FEATURE:
<223> OTHER INFORMATION: synthesized peptide sequences selected from a
      phage display library

<400> SEQUENCE: 50

Arg Phe Pro Gly Pro Ile Glu Pro Asp Leu Arg Phe
1               5                   10

<210> SEQ ID NO 51
<211> LENGTH: 12
<212> TYPE: PRT
<213> ORGANISM: Artificial
<220> FEATURE:
<223> OTHER INFORMATION: synthesized peptide sequences selected from a
      phage display library

<400> SEQUENCE: 51

Trp Ser Pro Ile Cys Gly Lys Phe Phe Gln Arg Phe
1               5                   10

<210> SEQ ID NO 52
<211> LENGTH: 13
<212> TYPE: PRT
<213> ORGANISM: Artificial
<220> FEATURE:
<223> OTHER INFORMATION: synthesized peptide sequences selected from a
      phase display library
<220> FEATURE:
<221> NAME/KEY: misc_feature
<222> LOCATION: (3)..(9)
<223> OTHER INFORMATION: Xaa can be any naturally occurring amino acid

<400> SEQUENCE: 52

Ala Cys Xaa Xaa Xaa Xaa Xaa Xaa Xaa Cys Gly Gly Gly
1               5                   10

<210> SEQ ID NO 53
<211> LENGTH: 13
<212> TYPE: PRT
<213> ORGANISM: Artificial
<220> FEATURE:
<223> OTHER INFORMATION: synthesized peptide sequences selected from a
      phage display library

<400> SEQUENCE: 53

Ala Cys Ser Trp Trp Ser Ile His Leu Cys Gly Gly Gly
1               5                   10

<210> SEQ ID NO 54
<211> LENGTH: 13
<212> TYPE: PRT
<213> ORGANISM: Artificial
<220> FEATURE:
<223> OTHER INFORMATION: synthesized peptide sequences selected from a
      phage display library

<400> SEQUENCE: 54

Ala Cys Asn Ala Gly His Leu Ser Gln Cys Gly Gly Gly
1               5                   10

<210> SEQ ID NO 55
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 55

Val His Trp Asp Phe Arg Gln Trp
1               5

<210> SEQ ID NO 56
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 56

Phe Arg Gln Trp Trp Gln Pro Ser
1               5

<210> SEQ ID NO 57
<211> LENGTH: 8
<212> TYPE: PRT

```
<213> ORGANISM: Artificial
<220> FEATURE:
<223> OTHER INFORMATION: synthesized peptide sequences selected from a
      phage display library

<400> SEQUENCE: 57

Trp Asp Phe Arg Gln Trp Trp Gln
1               5

<210> SEQ ID NO 58
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 58

Leu Asn Phe Pro Met Pro Ser Arg
1               5

<210> SEQ ID NO 59
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 59

Met Pro Ser Arg Pro His Ser Ser
1               5

<210> SEQ ID NO 60
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 60

Phe Pro Met Pro Ser Arg Pro His
1               5

<210> SEQ ID NO 61
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 61

Gln Ser Leu Pro Trp Cys Tyr Pro
1               5

<210> SEQ ID NO 62
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 62

Trp Cys Tyr Pro His Cys Val Thr
1               5
```

```
<210> SEQ ID NO 63
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 63

Leu Pro Trp Cys Thr Pro His Cys
1               5

<210> SEQ ID NO 64
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 64

Trp Ser Pro Ile Ser Gly Lys Phe
1               5

<210> SEQ ID NO 65
<211> LENGTH: 7
<212> TYPE: PRT
<213> ORGANISM: Artificial
<220> FEATURE:
<223> OTHER INFORMATION: synthesized peptide sequences selected from a
      phage display library

<400> SEQUENCE: 65

Ser Gly Lys Phe Phe Gln Arg
1               5

<210> SEQ ID NO 66
<211> LENGTH: 8
<212> TYPE: PRT
<213> ORGANISM: Artificial
<220> FEATURE:
<223> OTHER INFORMATION: synthesized peptide sequences selected from a
      phage display library

<400> SEQUENCE: 66

Pro Ile Ser Gly Lys Phe Phe Gln
1               5
```